(12) United States Patent
Kuroda et al.

(10) Patent No.: US 7,951,379 B2
(45) Date of Patent: *May 31, 2011

(54) HOLLOW NANOPARTICLE OF NBSAG LARGE PROTEIN FOR DRUG DELIVERY

(75)

1 PARTICLE FORMATION SUPPRESSING SITE
2 DIRECT RECEPTOR SPECIFIC TO HUMAN HEPATOCYTE
3 SUGAR CHAIN 1
4 INDIRECT HUMAN HEPATOCYTE SPECIFIC RECEPTOR
  (POLYMERIZED HUMAN SERUM ALUBUMIN RECEPTOR)
5 TRANSMENBRANE REGION 1
6 TRANSMEMBRANE REGION 2
7 SUGAR CHAIN 2
8 TRANSMEMBRANE REGION 3

FIG. 13

| | |
|---|---|
| Pyrobest DNA POLYMERASE (TaKaRa) | 0.5 μl |
| 10×PCR BUFFER | 5 μl |
| dNTP MIXTURE (10mM) | 5 μl |
| TEMPLATE DNA(5 μg/ml) | 2 μl |
| PRIMER (F)(100 μM) | 1 μl |
| PRIMER (R)(100 μM) | 1 μl |
| DISTILLED WATER | 35.5 μl |
| TOTAL | 50 μl |

FIG. 14

| | CYCLE | TEMPERATURE | TIME |
|---|---|---|---|
| 1 | 1 | 98°C | 30 sec. |
| 2 | 30 | 98°C | 30 sec. |
| | | 55°C | 1 min. |
| | | 68°C | 30 min. |
| 3 | 1 | 4°C | ∞ |

FIG. 16 (a)    SUPERNATANT (×2 DILUTED)
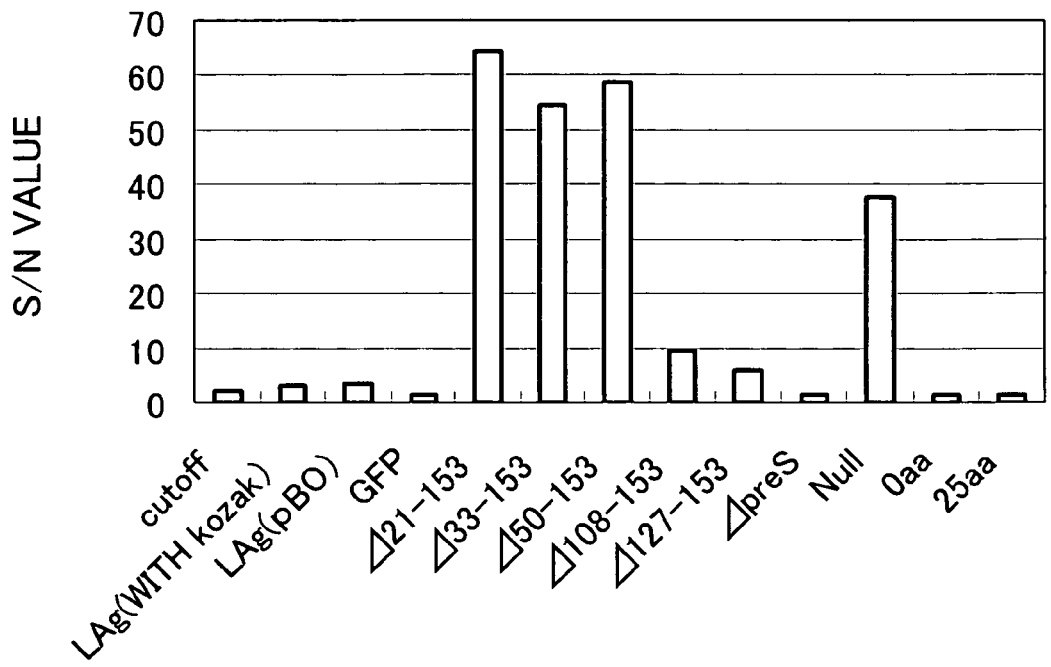
FIG. 16 (b)    CELLS (×200 DILUTED)
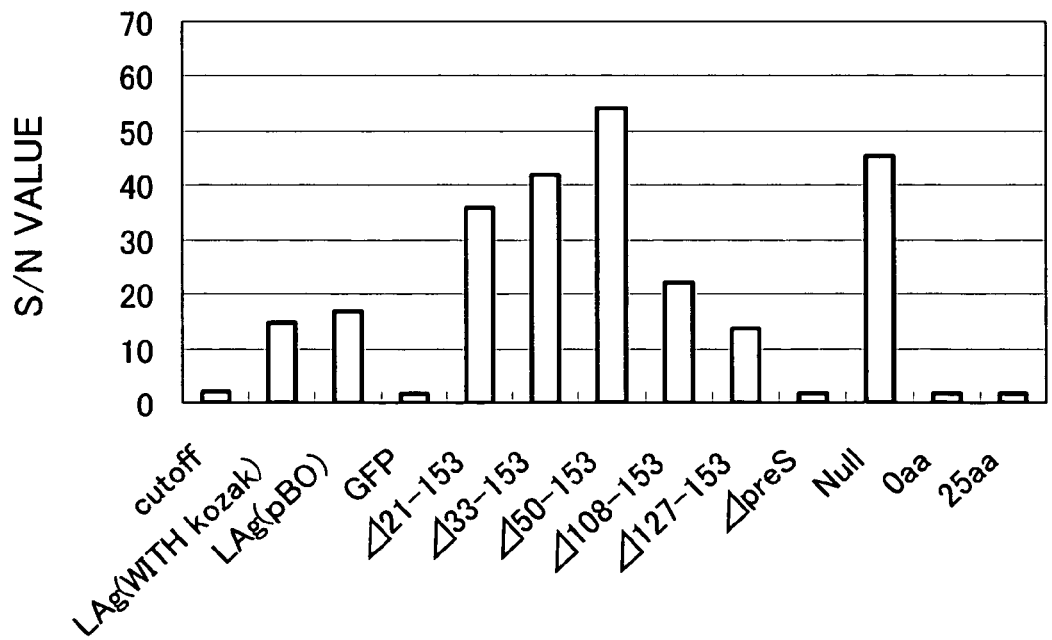

FIG. 17

|  | SUPERNATANT(×2 DILUTED) | | | CELLS (×200 DILUTED) | | |
|---|---|---|---|---|---|---|
| plasmid | S/N | RATE | DECISION | S/N | RATE | DECISION |
| LAg(WITH kozak) | 3.13 | 26.6 | R | 14.74 | 115.0 | R |
| LAg(pBO) | 3.68 | 31.3 | R | 17.00 | 132.6 | R |
| GFP | 1.41 | 12.0 |  | 1.69 | 13.2 |  |
| △21-153 | 64.54 | 548.6 | R | 35.79 | 279.2 | R |
| △33-153 | 54.39 | 462.3 | R | 42.03 | 327.8 | R |
| △50-153 | 58.67 | 498.7 | R | 54.19 | 422.7 | R |
| △108-153 | 9.58 | 81.4 | R | 22.32 | 174.1 | R |
| △127-153 | 5.93 | 50.4 | R | 13.73 | 107.1 | R |
| △preS | 1.52 | 12.9 |  | 1.59 | 12.4 |  |
| Null | 37.73 | 320.7 | R | 45.41 | 354.2 | R |
| 0aa | 1.42 | 12.1 |  | 1.65 | 12.9 |  |
| 25aa | 1.46 | 12.4 |  | 1.6 | 12.5 |  |

| STRAIN | S/N |
|---|---|
| LAg | 233 |
| ⊿21-153 | 255.03 |
| ⊿33-153 | 189.22 |
| ⊿50-153 | 318.45 |
| ⊿21-153+ZZ | ... |
| ⊿33-153+ZZ | 280.18 |
| ⊿50-153+ZZ | 304 |

FIG. 23

| | |
|---|---|
| PROTEINS ATTACKING CYTOPLASMIC RNA SUCH AS RNase | Pancreatic type Rnases from vertebrates |
| | RNase 1 or Bovine RNase A |
| | Eosinophil derived neurotoxin |
| | Eosinophil cationic protein |
| | Liver RNase (RNase 4) |
| | Angiogenin |
| | Bovine seminal RNase |
| | Frog Rnases (Onconase etc.) |
| PROTEINS OBSTRUCTING MEMBRANE TRANSPORT | Streptolysin(Streptococcus pyogenes) |
| | Cholesterol binding toxins (Streptococcus. Bacillus. Clostridium. Listeria) |
| | alpha-Toxin (Staphylococcus aureus) |
| | Delta-Toxin (Staphylococcus aureus) and melittin (Apis mellifera) |
| | Aerotysin (Aeromonas hydrophila) |
| | Escherichia coli hemolysin |
| PROTEINS OBSTRUCTING SIGNAL TRANSDUCTION | Cholera toxin (Vibrio cholerae) |
| | Heat-labile enterotoxins (Escherichia ColID) |
| | Pertussis toxin (Bordetella periussis) |
| | Exoenzyme C3 (Clostridium botulinum) |
| | Adenylate cyclase toxin (Bordetella sp.) |
| | Anthrax edema factor (Bacillus anthracis) |
| PROTEINS OBSTRUCTING PROTEIN SYNTHESIS | Diphtheria toxin (Corynebacterium diphtheriae) |
| | Pseudomonas aeruginosa exotoxin A |
| | Shiga toxins (Shigella dysenteriae serotype I, Escherichia Coli) |
| | Ricin (Ricinus communis) |
| | Ribosome-inactivating proteins |
| | alpha-Sarcin and related toxins (Aspergillus) |
| PROTEINS DISTURBING CYTOSKELTON | C2 toxin (Clostridium botulinum type C and D) |
| | Cytotoxic necrotizing factors (Escherichia coli) |
| | Enterotoxin A and cytotoxin B (Clostridium difficile) |
| | ActA (Listeria monocytogenes) |
| | IcsA (Shigella flexneni) |
| | Zonula occludens toxin (Vibrio cholerae) |

FIG. 24

| | |
|---|---|
| PROTEINS SUPPRESSING IMMUNITY OR INFLAMMATORY REACTION | Pyrogenic exotoxins (superantigens) (Staphylococcus aureus and Streptococcus pyogenes) |
| | Anthrax lethal toxin (Bacillus anthracis) |
| | Leukocidins and gamma lysins (Staphylococcus sp.) |
| PROTEINS DISTURBING MEMBRANE TRANSPORT | Tetanus neurotoxin (Clostridium tetani) |
| | VAMP-specific botulinum neurotoxins |
| | Botulinum neurotoxins type A and E (Clostridium botulinum) |
| | Botulinum neurotoxin type C (Clostridium botulinum) |
| | Vacuolating cytotoxin (Helicobacter pylonD |
| Na CHANNEL DISTURBING PROTEINS | alpha-Scorpion toxins |
| | beta-Scorpion toxins |
| | Excitatory insect selective neurotoxins from scorpion venoms |
| | Depressant insect selective neurotoxins from scorpion venoms |
| | mu-Conotoxins (Conus geographus) |
| | mu-Agatoxins (Agelenopsis aperta) |
| | Anthopleurin-A. -B, and -C (anemone toxin) |
| | Anemone toxins (type II) |
| | Calitoxins |
| K CHANNEL DISTURNING PROTEINS | Kaliotoxin |
| | Scyllatoxin (Leiurus quinquestriatus hebraeus) |
| | Apamin (honey bee Apis mellifera) |
| | MCD peptide (honey bee Apis mellifera) |
| | Charybdotoxin and iberiotoxin (Leiurus quinquestriatus var. hebraeus and Buthus tamul us) |
| | Margatoxin, noxiustoxin, and kaliotoxin (Centruroides margaritatus. Centruroides noxius, Androctonus mauretanicus) |
| | Dendrotoxins (Dendroaspis species) |
| | Sea anemone potassium channel toxins |

FIG. 25

| Ca CHANNEL DISTURBING PROTEINS | Omega-Conotoxins (Conus spp.) |
|---|---|
| | Omega-Agatoxins (Agelenopsis aperta) |
| | Omega-Grammotoxin SIA (Grammostola spatulata Chilean pink tarantula) |
| | Hololena toxin (Hololena curta) |
| | PLTXII (Plectreurys tristes) |
| | Calciseptine (Dendroaspis polylepis) |
| | Calcicludine (Dendroaspis angusticeps) |
| | beta-Leptinotarsin-h |
| | Taicatoxin (Oxyuranus scutelatus scutelatus) |
| ACETYLCHOLINE RECEPTOR DISTURBING PROTEINS | alpha-Bungarotoxin (Bungarus multicinctus) |
| | alpha-Cobratoxin (Naja kaouthia) |
| | Erabutoxins (Laticauda semifasciata) |
| | Toxin alpha ('Naja nigricollis') |
| | kappa-Bungarotoxin (Bungarus multicinctus) |
| | alpha-Conotoxins (Conus spp.) |
| | Snake toxins against muscarinic acetylcholine receptors |
| | Muscarinic toxin-1~-5, -7, m1-toxin from green mamba (Dendroapsis angusticeps) |
| | Muscarinic toxin-alpha, -beta from black mamaba (Dendroapsis polylepis) |
| RYANODINE RECEPTOR $Ca^{2+}$ CHANNEL DISTURBING PROTEINS | Helothermine (Heloderma horridum horridum) |

FIG. 26

| PRESYNAPTIC DISTURBING PROTEINS | PRESYNAPTIC DISTURBING PROTEINS |
|---|---|
| | Rattlesnake venom neurotoxins: crotoxin-related proteins |
| | Ammodytoxins (Vipera ammodytes ammodytes) |
| | Notexins (Notechis scutatus scutatus) |
| | Textilotoxin (Pseudonaja textilis textilis) |
| | Tai poxin |
| | alpha-Latrotoxin (black widow spider) |
| | alpha-Latroinsectotoxin (Latrodectus mactans tred ecimguttatus) |
| | Pardaxin (Pardachirus marmoratus) |
| | Palytoxin (Corals of the spp. Palythoa) |
| | Equinatoxins (Actinia equina L., sea anemone) |
| GLUTAMIC ACID RECEPTOR DISTURBING PROTEINS | Conantokins (Conus spp.) |

FIG. 27

| | | TIME AFTER GCV ADMINISTRATION (DAYS) | | | | | | |
|---|---|---|---|---|---|---|---|---|
| | | 0 | 1 | 3 | 6 | 9 | 1 2 | 1 5 |
| TUMOR SIZE (%) | A 4 3 1 | 100 | 102 | 97 | 94 | 85 | 72 | 66 |
| | W i D r | 100 | 105 | 107 | 111 | 118 | 125 | 133 |

HOLLOW NANOPARTICLE OF NBSAG LARGE PROTEIN FOR DRUG DELIVERY

TECHNICAL FIELD

The present invention relates to therapeutic drugs using antibody-displaying hollow protein nanoparticles, and to hollow protein nanoparticles. The invention particularly relates to a drug whose particle surface displays bio-recognizing molecules such as an antibody against a specific cell or tissue, and which contains particles encapsulating a substance to be transferred into a cell for treating a disease, wherein the drug allows the disease-treating substance to be specifically incorporated into a specific cell or tissue. The invention also relates to particles suitable for the drug.

BACKGROUND ART

In the field of medicine, there has been active research on drugs that directly and effectively act on the affected area without causing serious side effects. One area of active research is a method known as a drug delivery system (DDS), in which active ingredients of drugs or other substances are specifically delivered to a target cell or tissue, where they can exhibit their effects.

Another area of active research is a technique of gene transfer to a specific cell, which is now essential in the field of molecular cell biology. With the genetic background of various diseases being revealed by the Human Genome Project, a method of highly specific gene transfer to a specific cell or tissue holds great promise because, once the method is established, it is applicable to the field of gene therapy.

In one known example of a gene transfer method to cells, uptake of genes takes place in the form of a giant molecule by endocytosis (calcium phosphate method, lipofectamin method). In another method, genes are transferred through cell membrane pores that are formed by the stimulation of the cell membrane with an electrical pulse (electroporation method, gene gun method). Both of these methods are commonly used in molecular biology experiments.

Despite the simplicity of these methods, they cannot be readily applied to cells or tissues of internal body, because the methods involve direct physical contact with the cells and surgically expose the site of gene transfer. It is also difficult to achieve near 100% uptake.

A transfer method that is safe to use is a liposome method. The liposome method does not damage the cell and is applicable to cells or tissues of internal body. A problem of the method, however, is that the liposome, which is a simple lipid, cannot have a high level of specificity to the cells or tissues, and uptake of genes in vivo is far below the required level.

In a recently developed technique, a therapeutic gene is inserted in viral DNA, and the gene is transferred by an infectious virus. The method is innovative in the sense that it does not expose the site of transfer, is applicable to individuals, and provides near 100% uptake. However, the method suffers from a serious drawback in that the virus non-specifically infects a wide range of cells, transferring the gene to cells other than the target cell. Further, the method has a potential risk of unexpected side effect if the viral genome is incorporated in the chromosomes. In fact, the method is not used in initial stages of disease treatment. Only the terminal patients can receive the benefit of the method.

In sum, none of the conventional gene transfer methods is sufficient to specifically transfer genes to a target cell and express the protein therein to produce a drug. To this date, there has been no effective method of directly delivering a protein as a drug into a target cell or tissue.

Under these circumstances, the inventors of the present invention have previously proposed a method of specifically and safely delivering and transferring various substances (including genes, proteins, compounds) into a target cell or tissue, using hollow nanoparticles of a protein that has the ability to form particles and has incorporated a bio-recognizing molecule, as disclosed in International Publication with International Publication No. WO01/64930 (published on Sep. 7, 2001) (hereinafter referred to as "International Publication WO01/64930"), and in Japanese Publication for Unexamined Publication No. 316298/2001 (published on Nov. 13, 2001). However, these publications do not fully discuss how the method can be used to develop drugs for the treatment of diseased cells or tissues (cancer, for example). Specifically, the development of drugs displaying a specific antibody for specific cancer cells or tissues remains to be one of the most important goals to be achieved, particularly in view of the following problems.

Owning to the difficulty in specifically and safely delivering and transferring a protein (drug) into a target cell or tissue, a great burden has been put on the patients receiving treatment using such a protein drug.

For example, for the treatment of viral hepatitis (hepatitis C in particular), an interferon, which is one form of a protein drug, is administered systemically through intravenous injection over an extended time period. Though the effectiveness of the treatment is well recognized, it has many side effects due to the non-specific action of the interferon, including high fever, loss of hair, tiredness, and immune response, which occur every time the drug is administered.

The hepatocyte growth factor is known to be effective for the treatment of liver cirrhosis. However, since systemic administration of the drug through intravenous injection may cause unexpected side effects, the hepatocyte growth factor is directly administered to the liver with a catheter. The use of catheter requires surgery, which puts a burden on the patient if he or she must receive prolonged treatment.

The present invention was made in view of the foregoing problems, and an object of the invention is to provide a therapeutic drug, proved to be effective by animal testing, that specifically acts on a target cell or tissue with its hollow protein nanoparticles displaying bio-recognizing molecules such as an antibody. The invention also provides a therapeutic method, and hollow nanoparticles for use in such a therapeutic drug and therapeutic method.

DISCLOSURE OF INVENTION

The inventors of the present invention accomplished the present invention by successfully preparing different types of hollow protein nanoparticles displaying an antibody, and by finding that hollow nanoparticles displaying an antibody specific to the human squamous carcinoma cell was effective in the treatment of transplanted cancer when a drug encapsulating a cancer treating gene in the hollow nanoparticles was administered in laboratory animals through intravenous injection.

That is, the present invention discloses a drug in which a substance to be transferred into a cell for treating a disease is encapsulated in hollow nanoparticles of a protein-forming protein displaying an antibody against a specific cell or specific tissue.

An example of such a protein is a hepatitis B virus surface-antigen protein that has been modified to lose its infectivity to the hepatocytes and display an antibody. In eukaryotic cells, the protein is expressed as a membrane protein on the endoplasmic reticulum and accumulates thereon before it is released as particles into the lumen. With the antibody displayed on the particle surface, the hollow nanoparticles can act as a carrier, delivering the substance encapsulated in the particles specifically to a specific cell or specific tissue. As used herein, "specific cell or specific tissue" refers to cells into which the substance encapsulated in the particles is introduced by the binding of the antibody with an antigen displayed on the cell surface, or tissues as a collection of such cells into which the substance is introduced.

The pre-S regions (pre-S1, pre-S2) of the hepatitis B virus surface-antigen protein have important roles in the binding of HBV to the hepatocytes. Thus, the hepatitis B virus surface-antigen protein can be modified to lose its infectivity to the hepatocytes by deleting some of the amino acids in the pre-S regions. In this way, the substance in the particles can also be introduced into cells or organs other than the liver.

When some of the amino acids in the pre-S region are deleted to remove the infectivity of the protein to the hepatocytes, the level of expression of the modified hepatitis B virus surface-antigen protein in the eukaryotic cell varies depending on the deleted area of pre-S region. The level of protein expression in the eukaryotic cell tends to decrease particularly when the protein is modified to display an antigen.

It is therefore preferable, in order to maintain a sufficient level of protein expression in the eukaryotic cell, that the protein (in the case of serotype y) be modified to retain at least N-terminal amino acid residues 1 to 20 in the entire amino acid sequence of the pre-S region (pre-S1, pre-S2 regions), or more preferably the protein be modified by deleting N-terminal amino acids 50 to 153 in the entire amino acid sequence of the pre-S region. For serotype d, the protein is preferably modified to retain at least N-terminal amino acid residues 12 to 31, or more preferably the protein is modified by deleting N-terminal amino acids 61 to 164 in the entire amino acid sequence of the pre-S region.

In this way, the hepatitis B virus surface-antigen protein modified to lose its infectivity to the hepatocytes and display an antibody is expressed in large amounts in the eukaryotic cell. With the increased amount of protein, more substance in the protein can be transported into specific cells or tissues, thereby greatly enhancing the effectiveness of the substance.

An example of the antibody is a cancer specific antibody or an anti-virus protein antibody. For example, a cancer treating substance (medicament) may be encapsulated in the hollow nanoparticles displaying a cancer-specific antibody. This provides an effective therapeutic drug that specifically and effectively acts on cancer cells. The anti-virus protein antibody is effective in the removal of virus-infected cells.

The antibody has a single chain or double chain. Due to its structure, the double chain antibody cannot readily be displayed on the particle surface by directly fusing it with the particle-forming protein. The inventors of the present invention found ways to successfully display the double chain antibody on the surface of the hollow nanoparticles by indirectly binding the double chain antibody to the protein. Specifically, the double chain antibody was displayed on the particle surface by first introducing a ZZ tag into the protein (fused with the protein), wherein the ZZ tag specifically binds to the Fc site of the double chain antibody, and then by ligating the ZZ tag to the Fc site. Another way to display the double chain antibody on the particle surface is to introduce a streptag into the protein (fused with the protein), wherein the streptag specifically binds to streptavidin (or its derivative), and bind the streptag to the streptavidin (or its derivative). The double chain antibody, which has been modified by biotin that specifically binds to the streptavidin (or its derivative), can then be displayed on the particle surface by ligating the streptavidin (or its derivative) to the biotin attached to the double chain antibody. The single chain antibody can be displayed on the particle surface by expressing it with the protein directly fused with the antibody.

Other than these methods, the antibody may be displayed on the particle surface by common binding methods involving chemical modification.

The hollow protein nanoparticles are preferably the product of expression in eukaryotic cells. The eukaryotic cell may be obtained from yeasts, insects, or animals including mammals.

The target-cell substance encapsulated in the hollow nanoparticles may be a cancer treating gene, for example. When the cancer treating gene encapsulated in the drug is a thymidine kinase (HSV1tk) gene derived from simple herpes virus, ganciclovir is additionally administered, as will be described in Examples.

The present invention discloses a drug that can be used by a convenient method of intravenous injection to effectively treat specific diseased cells or tissues. The drug is a great leap forward from conventional disease treatment methods in that it does not require large dose or any surgical operation in disease treatment including gene therapy, and that the risk of side effect is greatly reduced. The drug is therefore usable in clinical applications in its present form.

The present invention discloses a treatment method for treating diseases through administration of the drug disclosed in the present invention.

The present invention discloses hollow nanoparticles of a hepatitis B virus surface-antigen protein of serotype y, the hepatitis B virus surface-antigen protein forming particles and being modified to retain at least N-terminal amino acid residues 1 to 20 in the entire amino acid sequence of the pre-S region. Preferably, the protein is modified by deleting N-terminal amino acids 50 to 153 in the entire amino acid sequence of the pre-S region.

The present invention discloses hollow nanoparticles of a hepatitis B virus surface-antigen protein of serotype d, the hepatitis B virus surface-antigen protein forming particles and being modified to retain at least N-terminal amino acid residues 12 to 31 in the entire amino acid sequence of the pre-S region. Preferably, the protein is modified by deleting N-terminal amino acids 61 to 164 in the entire amino acid sequence of the pre-S region.

The hollow nanoparticles are expressed in large amounts particularly in the eukaryotic cell, and are suitable for displaying bio-recognizing molecules. For example, the hollow nanoparticles may be used as hollow bio-nanoparticles in gene therapy or DDS.

For a fuller understanding of the nature and advantages of the invention, reference should be made to the ensuing detailed description taken in conjunction with the accompanying drawings.

BRIEF DESCRIPTION OF DRAWINGS

FIG. 13 is a diagram showing reaction compositions of PCR as described in Examples of the present invention.

FIG. 14 is a diagram showing a PCR cycle as described in Examples of the present invention.

FIGS. 16(a) and 16(b) are graphs showing results of enzyme immunoassay performed on deletion HBsAg protein in animal cells as described in Examples of the present invention, wherein FIG. 16(a) is a result in supernatant, and FIG. 16(b) is a result in cells.

FIG. 17 is a diagram representing the results of FIGS. 16(a) and 16(b) in data form.

FIG. 23 is a diagram listing examples of target-cell substances according to the present invention.

FIG. 24 is a diagram listing examples of target-cell substances according to the present invention.

FIG. 25 is a diagram listing examples of target-cell substances according to the present invention.

FIG. 26 is a diagram listing examples of target-cell substances according to the present invention.

FIG. 27 is a table representing a result of treatment on laboratory animals using a drug according to the present invention.

BEST MODE FOR CARRYING OUT THE INVENTION

The present invention discloses a drug including hollow nanoparticles whose particle surface displays an antibody as a bio-recognizing molecule (molecule that recognizes a specific cell), and which contains particles encapsulating a substance to be transferred into a cell for treating a disease, wherein the drug allows the disease-treating substance to be specifically delivered to a target cell or tissue. The hollow nanoparticles may be a protein able to form particles, which may be sub viral particles obtained from various viruses. Specific examples of such a protein include hepatitis B virus (HBV) surface-antigen protein.

Particles of such a protein may be obtained through the protein expression in the eukaryotic cell. Specifically, in eukaryotic cells, the particle-forming protein is expressed on the endoplasmic reticulum as a membrane protein and accumulates thereon before it is released as particles. The eukaryotic cell may be obtained from yeasts, insects, or animals including mammals.

As will be described later in Examples, the inventors of the present invention have reported that the expression of HBV surface-antigen L protein in recombinant yeast cells produces ellipsoidal hollow particles with a minor axis of 20 nm and a major axis of 150 nm, with a large number of L proteins embedded in the yeast-derived lipid bilayer membrane (J. Biol. Chem., Vol. 267, No. 3, 1953-1961, 1992). The particles contain no HBV genome and lack the viral function. Therefore, the particles are very safe to the human body.

The HBV surface-antigen L protein may be modified to lack its infectivity to the hepatocytes and display an antibody (cancer specific antibody, for example) on the particle surface. With the antibody on the particle surface of the expressed protein, the protein can effectively serve as a carrier for specifically delivering substances to cells or tissues (cancer cell or cancer tissue in the case of a cancer specific antibody) whose cell surface has an antigen against the antibody.

Figure 1:
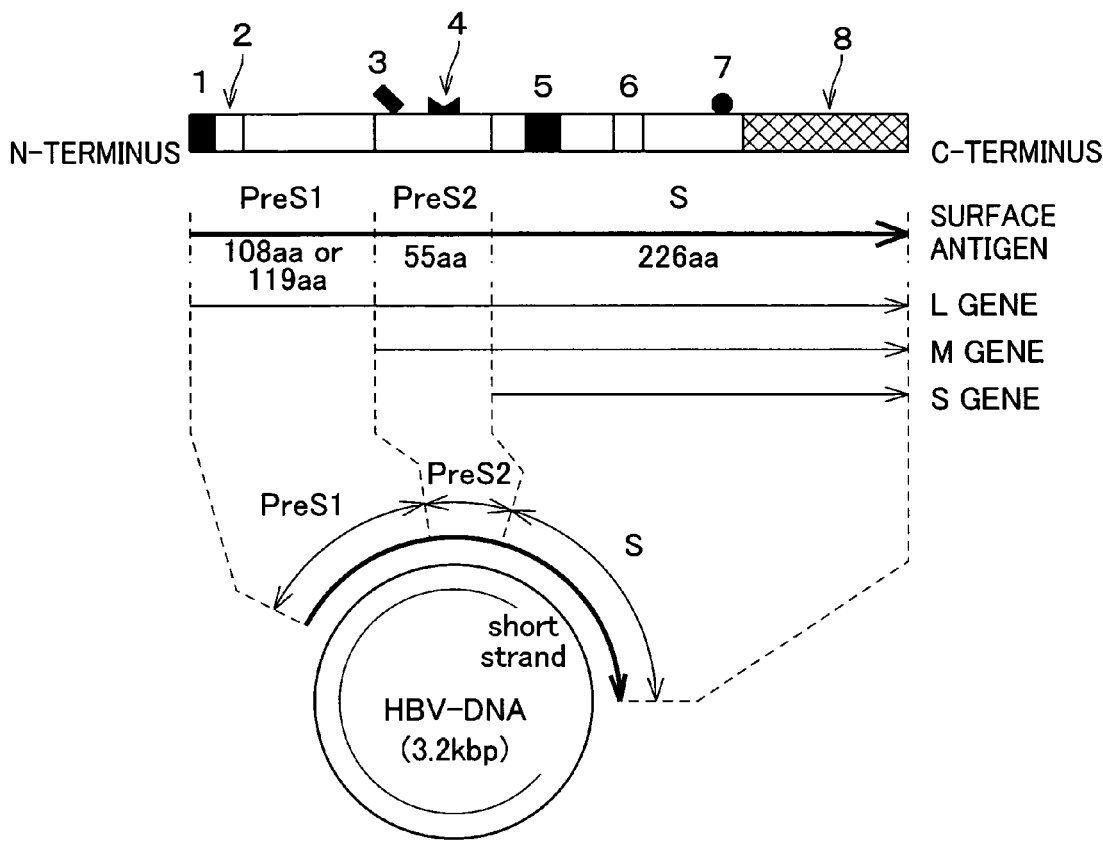
FIG. 1 is a schematic diagram showing protein regions of HBsAg gene described in Examples of the present invention, where the numbers 1 through 8 indicate respective functions of different sites on a surface antigen, and Pre-S1 indicates 108 amino acid residues for serotype y, and 119 amino acid residues for serotype d.

The pre-S regions (pre-S1, pre-S2) of the HBV surface-antigen L protein have important roles in the binding of HBV to the hepatocytes (see FIG. 1). Thus, the HBV surface-antigen L protein can be modified to lose its infectivity to the hepatocyte by deleting some of the amino acids in the pre-S regions. As used herein, "deletion of some of the amino acids in the pre-S region" means deleting some of the amino acids in the preS1 region or preS2 region, or both of these regions. For example, infectivity to the hepatocytes can be lost by deleting N-terminal amino acids 3 to 66 (serotype y) or N-terminal amino acids 4 to 77 (serotype d), known as a recognition site for the human hepatocytes, in the pre-S region (specifically PreS1 region).

When the protein is modified to lose its infectivity to the hepatocytes by deleting at least some of the amino acids in the pre-S region, the level of protein expression in the eukaryotic cell varies in the modified hepatitis B virus surface-antigen protein, depending on the region of amino acid deleted. The level of protein expression is prone to decrease particularly when the protein is modified to display antigens.

The modified hepatitis B virus surface-antigen protein can be expressed in a large amount in the eukaryotic cell when amino acids in the pre-S region are deleted in domain, as will be described in Examples. Specifically, as noted above, the level of protein expression in the eukaryotic cell can be increased by deleting N-terminal amino acids 3 to 66 (serotype y) or N-terminal amino acids 4 to 77 (serotype d), known as a recognition site for the human hepatocytes, in the preS1 region. For serotype y, the protein may be modified to retain at least N-terminal amino acid residues 1 to 20. For serotype d, at least N-terminal amino acid residues 12 to 31 may be retained.

The level of protein expression can be further increased by preferably deleting some of the amino acids in the preS2 region, in addition to some of the amino acids making up the recognition site for the human hepatocytes in the preS1 region.

More specifically, it is preferable in the entire amino acid sequence in the pre-S region (pre-S1 region, pre-S2 region) that the protein be modified to delete N-terminal amino acids 50 to 153 and retain at least N-terminal amino acid residues 1 to 20. For example, for serotype y, it is preferable in the entire amino acid sequence of the pre-S region that the protein be modified to lack domains of amino acid in the first 153 amino acids from the N-terminus, specifically, from amino acids 50 to 153, 33 to 153, and 21 to 153, as will be described later in Examples. Among these domains, it is particularly preferable to delete amino acids 50 to 153. Note that, the deleted range of amino acid is not just limited to this example.

For serotype d, it is preferable in the entire amino acid sequence of the pre-S region (preS1 region, preS2 region) that the protein be modified to lack N-terminal amino acids 61 to 164 and retain at least N-terminal amino acid residues 12 to 31.

The hepatitis B virus surface-antigen protein so modified to lose its infectivity to the hepatocytes and display antibody is expressed in a large amount in the eukaryotic cell, and therefore is highly advantageous in terms of productivity. With the increased amount of protein, more substance in the protein can be transported into specific cells or tissues, thereby greatly enhancing the effectiveness of the substance.

Therefore, forming the protein particles using recombinant yeasts offers a preferable method of efficiently producing particles from soluble proteins in the yeasts.

The insect cell, being a eukaryote closer to some of the higher animals than the recombinant yeast, is able to form a higher order structure such as a sugar chain unachievable by yeasts. In this connection, the insect cell provides a preferable method of producing heteroproteins in large amounts. The conventional insect cell line used the baculovirus and involved viral expression. This has caused a cell death or lysis in the protein expression. A problem of this method, then, is that the protein expression proceeds continuously, or the proteins are decomposed by the free protease separated from the dead cells. Further, in the secretion and expression of proteins, inclusion of a large amount of fetal bovine serum contained in the culture medium has made it difficult to purify proteins even when proteins are secreted in the medium. In recent years, Invitrogen Corporation has developed and marketed an insect cell line that can be cultured without a serum and without being meditated by the baculovirus. Such an insect line can be used to obtain protein particles that are easy to purify and form into higher order structures.

Hollow protein nanoparticles of the present invention are prepared by binding an antibody to the surface of particles obtained by the foregoing methods. With various substances (DNA, RNA, proteins, peptides, drugs, etc.) incorporated into the particles, the hollow protein nanoparticles can very specifically deliver and transfer these substances to cells bearing corresponding antigens on its cell surface.

The particle-forming protein is not just limited to the modified hepatitis B virus surface-antigen protein. For example, animal cells, plant cells, viruses, natural proteins derived from fungi, and various types of synthetic proteins may be used. Further, when there is a possibility that, for example, virus-derived antigen proteins may trigger antibody reaction in a target organism, a particle-forming protein with suppressed antigenic action may be used. For example, such a protein may be the hepatitis B virus surface-antigen protein modified to suppress its antigenic action, or other types of modified proteins (hepatitis B virus surface-antigen protein modified by genetic engineering), as disclosed in International Publication WO01/64930.

The type of antibody bound to the particle surface is not particularly limited as long as it recognizes a surface molecule of a specific cell as an antigen. For example, the antibody may be a cancer specific antibody that recognizes a surface molecule of a specific cancer cell as an antigen. As another example, an antibody may be used that specifically recognizes an antigen on the surface of a specific cell as a growth factor receptor or cytokine receptor. Other than these examples, various types of antibodies specific to other types of antigens displayed on the cell surface or tissue surface may be used as well. Specifically, an anti-viral protein antibody may be used, in addition to the antibodies used in the Examples below. The antibody should be suitably selected according to the type of target cell or tissue.

As described, the present invention provides hollow protein nanoparticles that encapsulate a substance (target-cell substance) to be transferred into a target cell or tissue, and thereby provides a substance carrier (drug) having cell specificity. The substance carrier may encapsulate any substance including, for example, genes in the form of DNA or RNA, natural or synthetic proteins, oligonucleotides, peptides, drugs, and natural or synthetic compounds.

For example, human RNase1 or RNase3 may be used, as previously reported by the inventors of the present invention. Human RNase1 is documented in Jinno H, Ueda M, Ozawa S, Ikeda T, Enomoto K, Psarras K, Kitajima M, Yamada H, Seno M Life Sci. 1996; 58(21): 1901-8. Human RNase3 (also known as ECP (eosinophil cationic protein)) is documented in Mallorqui-Fernandez G, Pous J, Peracaula R, Aymami J, Maeda T, Tada H, Yamada H, Seno M, de Llorens R, Gomis-Ruth F X, Coll M; J Mol Boil. 2000 Jul. 28; 300(5): 1297-307.

The proteins have cytotoxicity, the effects of which are both intracellular and extracellular. With the RNase encapsulated in the substance carrier (drug) of the present invention, the cytotoxicity of the protein can be masked outside the cell, and the protein exhibits its effect only inside the cell. It is expected that this will provide a novel cancer treatment method that causes fewer side effects.

Note that, the target-cell substance may be proteins shown in FIG. 23 through 26, or genes that encode these proteins. Other examples of the substance are various proteins including: cancer suppressor genes (p53, etc.); interferons; interleukins; cytokines; colony stimulating factors; tumor necrosis factors; transforming growth factors β; platelet-derived growth factors; erythropoietins; and Fas antigens. The target-cell substance may also be genes that encode these proteins.

These target-cell substances may be incorporated into the hollow nanoparticles by various methods commonly used in chemical or molecular biological experimental techniques. Some of the preferred examples include an electroporation method, ultrasonic method, simple diffusion method, and a method using charged lipids.

The hollow protein nanoparticles or substance carrier allow the substance to be specifically transported into cells or tissues in vivo or in vitro. Specific transport of the substance into a specific cell or specific tissue with the use of the hollow protein nanoparticles or substance carrier may be used as a treatment method of various diseases, or one of the steps in the procedure of the treatment method.

In a drug according to the present invention, the antibody may be displayed on the particle surface by four different methods, as will be described in the Examples. In the first method, a ZZ tag that specifically binds to an Fc site of a double chain antibody is incorporated into a particle-forming protein (in other words, particles are formed by expressing the protein with the ZZ tag fused with the protein), and the ZZ tag is bound to the Fc site to display the double chain antibody on the particle surface. In the second method, a streptag that specifically binds to streptavidin is incorporated into a particle-forming protein (in other words, particles are formed by expressing the protein with the streptag fused with the protein). The streptag is bound to the streptavidin (or its derivative), which is then bound to a double chain antibody that has been modified with biotin that specifically binds to the streptavidin (or its derivative), thereby displaying the antibody to the particle surface. In the third method, particles are formed by expressing the particle-forming protein with a single chain antibody fused with the protein, thereby displaying the antibody on the particle surface. The fourth method is chemical binding of the antibody with particles with the use of common crosslinking agents, which may be, for example, compounds including the NHS (N-hydroxysuccinimide) group, maleimide group, or imidoester group (available from Pierce Biotechnology, Inc.). These methods may be partly modified by taking advantage of their principles.

The effectiveness of the treatment using the drug of the present invention has been confirmed by animal testing, as will be described later in the Examples. In the Examples, cells derived from human squamous cell carcinoma were transplanted in nude rats, and the drug of the present invention and ganciclovir (GCV) were administered to each rat in separate doses. The drug on its particle surface had an antibody that recognizes an antigen, the epidermal growth factor (EGF receptor), expressed by the cancer cells. Inside the drug, a thymidine kinase (HSV1tk) gene derived from simple herpes virus was encapsulated. The effectiveness of the treatment was confirmed by observing the size of grafted cancer tissue. The drug was administered intravenously. However, oral administration, intramuscular administration, intraperitoneal administration, subcutaneous administration, or other administration routes are also available.

In the following, the present invention will be described in more detail by way of Examples with reference to the attached drawings. It should be appreciated that the present invention is not limited in any ways by the following Examples, and various modifications to details of the invention are possible.

It should also be noted that the techniques described in the following Examples are all novel and were independently developed by the inventors of the present invention. The novel techniques include: incorporating a protein in the preS1 region of the deletion HBV surface-antigen L protein; producing a deletion HBV surface-antigen L protein suitable for efficient expression in the eukaryotic cell; incorporating a bio-recognizing molecule (antibody) in the deletion HBV surface-antigen L protein for displaying it on the deletion HBV surface-antigen L protein; and application of these techniques in gene therapy or DDS.

EXAMPLES

In the following, HBsAg refers to hepatitis B virus surface antigen. HBsAg is an envelope protein of HBV, and includes three kinds of proteins S, M, and L, as schematically illustrated in FIG. 1. S protein is an important envelope protein common to all three kinds of proteins. M protein includes the entire sequence of the S protein with additional 55 amino acids (pre-S2 peptide) at the N-terminus. L protein contains the entire sequence of the M protein with additional 108 amino acids (serotype y) or 119 amino acids (serotype d) at the N-terminus. In the following Examples, serotype y was used.

The pre-S regions (pre-S1, pre-S2) of HBV have important roles in the binding of HBV to the hepatocytes. The Pre-S1 region has a direct binding site for the hepatocytes, and the pre-S2 region has a polymeric albumin receptor that binds to the hepatocytes via polymeric albumin in the blood.

Expression of HBsAg in the eukaryotic cell causes the protein to accumulate as membrane protein on the membrane surface of the endoplasmic reticulum. The L protein molecules of HBsAg agglomerate and are released as particles into the ER lumen, carrying the ER membrane with them as they develop.

Figure 2:
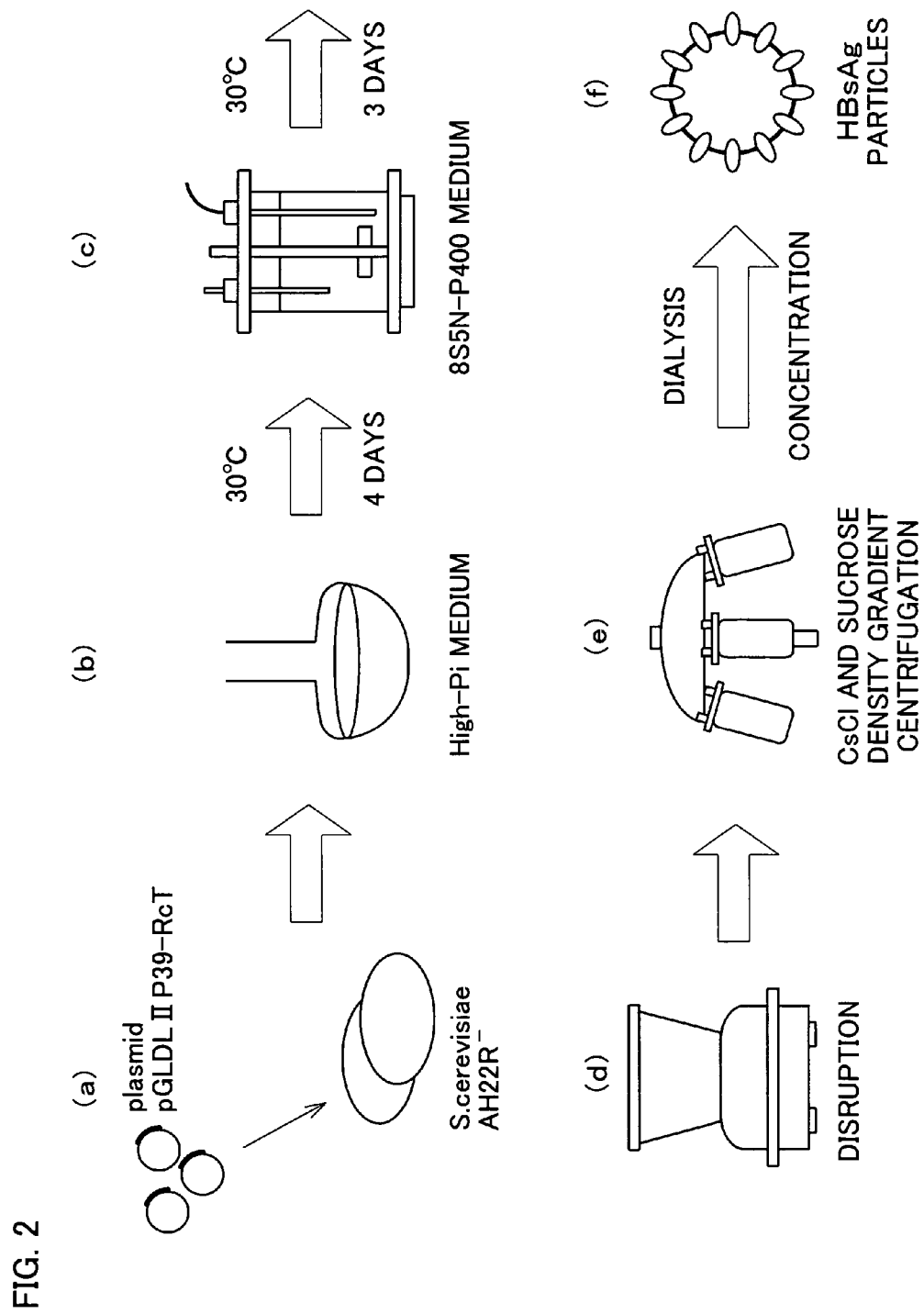
FIG. 2 is an explanatory drawing schematically showing one example of expression and purification procedures for HBsAg particles using recombinant yeasts, as described in Examples of the present invention, wherein (a) illustrates preparation of recombinant yeasts, (b) illustrates incubation in High-Pi medium, (c) illustrates incubation in 8S5N-P400 medium, (d) illustrates disruption, (e) illustrates density gradient centrifugation, and (f) illustrates HBsAg particles.

The Examples below used L proteins of HBsAg. FIG. 2 briefly illustrates procedures of expression and purification of HBsAg particles described in the following Examples.

Example A

Expression of HBsAg Particles in Recombinant Yeasts

Recombinant yeasts (*Saccharomyces cerevisiae* AH22R⁻ strain) carrying (pGLDLIIP39-RcT) were cultured in synthetic media High-Pi and 8S5N-P400, and HBsAg L protein particles were expressed (FIG. 2a through 2c). The whole procedure was performed according to the method described in J. Biol. Chem., Vol. 267, No. 3, 1953-1961, 1992 reported by the inventors of the present invention.

From the recombinant yeast in stationary growth phase (about 72 hours), the whole cell extract was obtained with the yeast protein extraction reagent (product of Pierce Chemical Co., Ltd.). The sample was then separated by sodium dodecyl sulfate-polyacrylamide gel electrophoresis (SDS-PAGE), and the HBsAg in the sample was identified by silver staining.

The result showed that HBsAg was a protein with a molecular weight of about 52 kDa.

Example B

Purification of HBsAg Particles from the Recombinant Yeasts (1) The recombinant yeast (wet weight of 26 g) cultured in synthetic medium 8S5N-P400 was suspended in 100 ml of buffer A (7.5 M urea, 0.1 M sodium phosphate, pH 7.2, 15 mM EDTA, 2 mM PMSF, and 0.1% Tween 80), and disrupted with glass beads by using a BEAD-BEATER. The supernatant was collected by centrifugation (FIG. 2d).

(2) The supernatant was mixed with a 0.75 volume of PEG 6000 solution (33%, w/w), and cooled on ice for 30 min. The pellets were collected by centrifugation at 7000 rpm for 30 min, and resuspended in buffer A without Tween 80.

(3) The solution was layered onto a 10-40% CsCl gradient, and ultracentrifuged at 28000 rpm for 16 hours. The centrifuged sample was divided into 12 fractions, and each fraction was tested for the presence of HBsAg by Western blotting (the primary antibody was the anti-HBsAg monoclonal antibody). The HBsAg fractions were dialyzed against buffer A without Tween 80.

(4) 12 ml of the dialyzed solution obtained in (3) was layered onto a 5-50% sucrose gradient, and ultracentrifuged at 28000 rpm for 16 hours. As in (3), the centrifuged sample was divided into fractions, and each fraction was tested for the presence of HBsAg. The HBsAg fractions were dialyzed against buffer A containing 0.85% NaCl, without urea or Tween 80 ((2) through (4): FIG. 2e).

(5) By repeating the procedure (4), the dizlyzed sample was concentrated with the ultrafilter Q2000 (Advantec), and stored at 4° C. for later use (FIG. 2f).

The result of Western blotting after CsCl equilibrium centrifugation in (3) revealed that HBsAg was a protein with S antigenicity with a molecular weight of 52 kDa. At the end of the procedure, about 24 mg of pure HBsAg particles were obtained from the yeast (26 g wet weight) derived from 2.5 L medium.

Each fraction obtained in the purification process was analyzed by SDS-PAGE. In order to confirm whether the purification had successfully removed the yeast-derived protease, the HBsAg particles obtained in (5) were incubated at 37° C. for 12 hours, separated by SDS-PAGE, and identified by silver staining.

The result of confirmation showed that the yeast-derived protease had been completely removed by the purification process.

The HBsAg particles specifically infect the human hepatocytes. The strong infectivity of the HBsAg particles is rendered by the hepatocyte recognition site displayed on the particle surface, which has been found on amino acid residues 3 to 77 in the pre-S1 region (Le Seyec J, Chouteau P, Cannie I, Guguen-Guillouzo C, Gripon P., J. Virol. 1999, March; 73(3): 2052-7).

In the following, description is made as to a producing method of the drug in which a cancer-specific antibody is displayed on the particle surface. In the producing method described below, the strong infectivity of the HBsAg particles to the hepatocytes has been removed in order to ensure that the drug of the present invention only acts on a specific cancer cell whose cell surface bears a molecule that is recognized as an antigen by the drug antibody. Further, the drug of the present invention was prepared in three different forms: (1) HBsAg particles displaying a cancer-specific antibody with a streptag; (2) HBsAg particles displaying a cancer-specific antibody with a ZZ tag; and (3) HBsAg particles displaying a cancer-specific single chain antibody expressed with the HBsAg protein fused with the antibody.

Example C

Preparation of HBsAg Particles Displaying a Cancer-Specific Antibody using a Streptag Example C-1

Preparation of HBsAg-Streptag Particles in Yeast Cells

In order to delete a gene region that encodes a human hepatocyte recognition site of the pGLDLIIP39-RcT plasmid discussed in Example A and at the same time insert a restriction enzyme NotI site (gcggccgc), PCR was run for the pGLDLIIP39-RcT plasmid using the oligonucleotides of SEQ ID NOs: 1 and 2 as PCR primers. The PCR was carried out with the QuickChange™ Site-Directed Mutagenesis Kit (Stratagene).

Specifically, using Pfu DNA polymerase (Stratagene) as a heat-resistant DNA polymerase, PCR was run in 30 cycles as follows: 30 second denature at 95° C., 1 minute annealing at 55° C., and 30 minute synthesis at 68° C. The PCR product was treated with restriction enzyme DpnI and transformed into E. coli DH5α. Then, vector DNA was extracted from the resultant colonies, and the extract was screened for mutant pGLDLIIP39-RcT plasmid based on the base sequence. In the following, the resultant plasmid will be called pGLDLIIP39-RcT-Null plasmid. Note that, in FIG. 3 and the subsequent drawings, a gene region of plasmid encoding HBsAg L protein that lacks the human hepatocyte recognition site will be denoted by "Null." For convenience of explanation, such a gene region will be called a "Null region."

Figure 3:
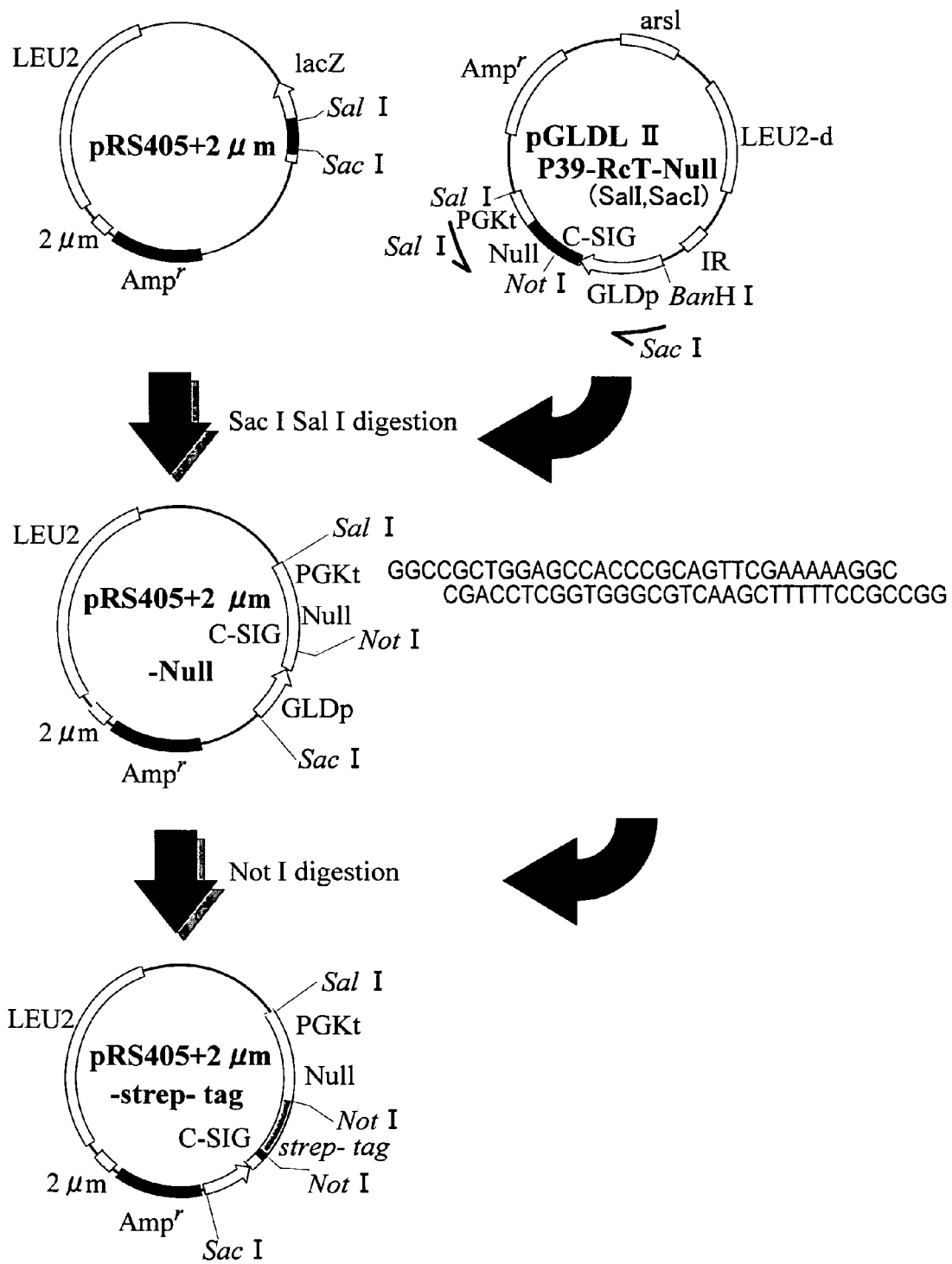
FIG. 3 is a diagram showing steps of constructing a plasmid used for preparation of HBsAg-streptag particles with yeasts, as described in Examples of the present invention.

In order to add a SacI site and SalI site in the pGLDLIIP39-RcT-Null plasmid, PCR was run using the oligonucleotides of SEQ ID NOs: 3 and 4 as PCR primers, as shown in FIG. 3, wherein the oligonucleotides of SEQ ID NOs: 3 and 4 had a SacI site and a SalI site, respectively. The PCR amplified the Null region, which contained a promoter (GLDp) and a terminator (PGKt), and cDNA fragments including the Null region were obtained.

Then, a pRS405+2 μm plasmid, which was prepared by inserting a 2 μm origin into AatII site of a universal yeast vector pRS405 (Stratagene), was digested with restriction enzymes SacI and SalI. The DNA fragments including the Null region were then inserted into the cleaved pRS405+2 μm plasmid, so as to prepare a pRS405+2 μm-Null plasmid.

Thereafter, synthetic oligonucleotides (oligonucleotide of SEQ ID NO: 5, and oligonucleotide of SEQ ID NO: 6 complementary to SEQ ID NO: 5) that encode a streptag were annealed and inserted into pRS405+2 μm-Null plasmid digested with NotI. As a result, a pRS405+2 μm-streptag plasmid was prepared that included a gene region encoding the streptag. The streptag is a peptide that binds to streptavidin with strong affinity like biotin, and has the sequence (1) SAWRHPQFGG (SEQ ID NO: 27) or (2) WSHPQFEK (SEQ ID NO: 28) from the N-terminus. Sequence (1) functions at the C-terminus of the protein. The present Examples used the streptag of sequence (2).

The pRS405+2 μm-streptag plasmid was used to transform yeasts (Saccharomyces cerevisiae AH22R⁻ strain). The resultant transformants were cultured, and the cultured cells were purified to obtain modified HBsAg particles (particles obtained by expressing the streptag fused with the HBsAg L protein lacking the human hepatocyte recognition site; hereinafter referred to as HBsAg-streptag particles) according to the method described in Example B. At the end of the procedure, about 200 μg of pure HBsAg-streptag particles were obtained from the yeasts derived from 1.0 L medium.

Example C-2

Preparation of HBsAg-Streptag Particles in Insect Cells in Serum-Free Medium

Example below describes a producing method of HBsAg-strept-tag particles using insect cell lines that can be cultured serum-free without the mediation of baculovirus. With the producing method using insect cell lines, a higher order structure such as a sugar chain can be realized.

Figure 4:
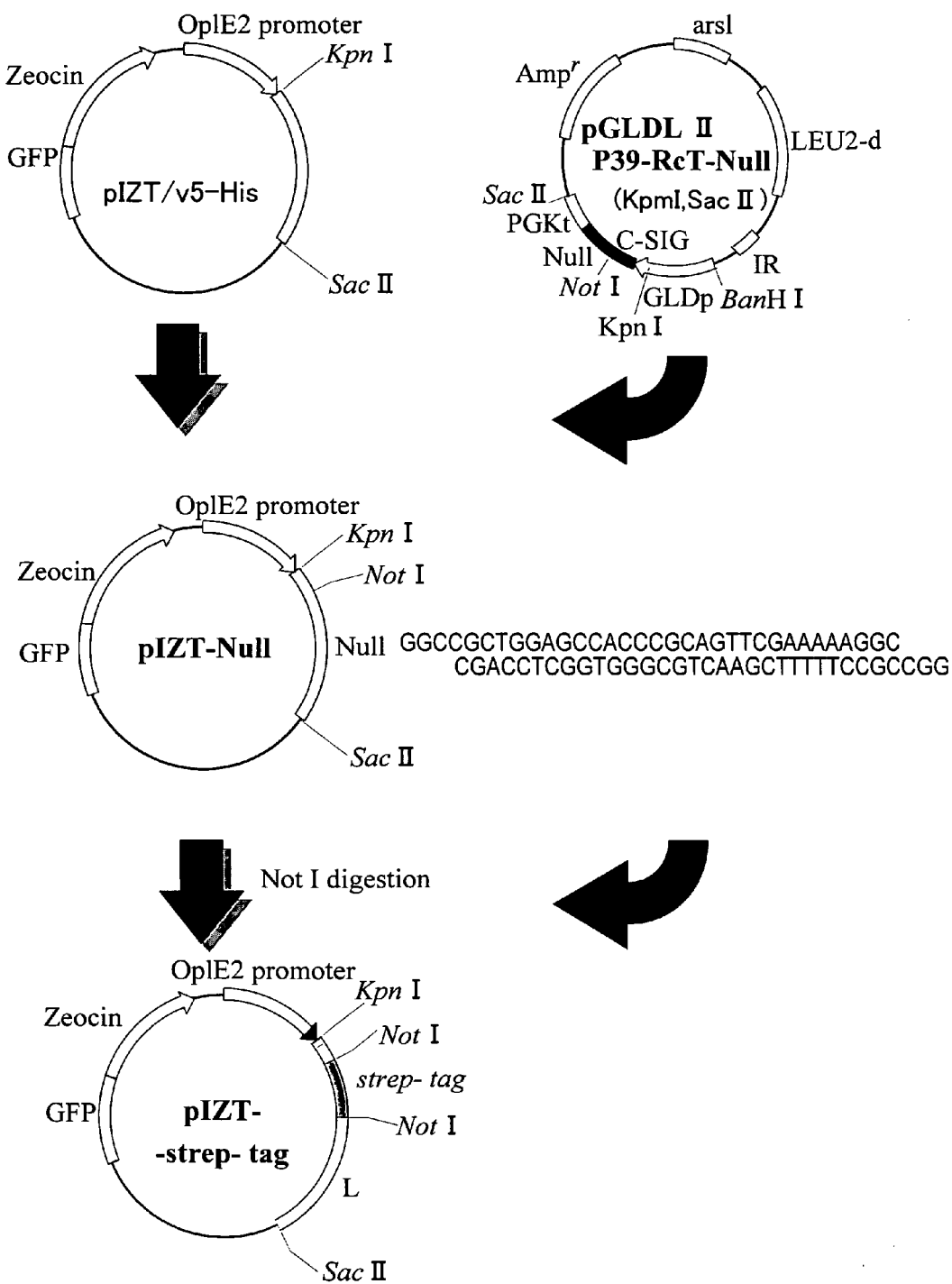
FIG. 4 is a diagram showing steps of constructing a plasmid used for preparation of HBsAg-streptag particles with insect cells, as described in Examples of the present invention.

As shown in FIG. 4, PCR was run for the pGLDLIIP39-RcT-Null plasmid obtained in Example C-1, using the oligonucleotides of SEQ ID NO: 7 and SEQ ID NO: 8 as PCR primers, wherein the oligonucleotides of SEQ ID NO: 7 and SEQ ID NO: 8 had a kpni site (ggtacc) and a SacII site (ccgcgg), respectively. The PCR amplified the Null region, which contained a coding region for a lysozym-secreted signal peptide derived from chicks.

The PCR product was electrophorased on agarose, and gene fragments of a target band about 1.3 kbp were collected. The gene fragment was ligated between the kpni site and SacII site of vector pIZT/V5-His (used for stable expression in insect cells) (Invitrogen Corporation) to close the ring, using TaKaRa Ligation kit ver. 2 (TaKaRa). The base sequence was confirmed, and the plasmid was named pIZT-Null.

Thereafter, as in Example C-1, synthetic oligonucleotides (oligonucleotide of SEQ ID NO: 5, and oligonucleotide of SEQ ID NO: 6 complementary to SEQ ID NO: 5) that encodes a streptag were annealed and inserted into the pIZT-Null plasmid digested with NotI. As a result, a pIZT-streptag plasmid was prepared that included a gene region encoding the streptag.

Meanwhile, the insect cell High Five line (BTI-TN-5B1-4): (Invitrogen Corporation) was slowly conditioned from the fetal bovine serum-contained medium to a serum-free medium (Ultimate Insect Serum-Free Medium: Invitrogen Corporation) over a period of about 1 month. Then, using the gene transfer lipid Insectin-Plus (Invitrogen Corporation), the pIZT-streptag plasmid was transferred for the transformation of the High Five line conditioned to the serum-free medium. The sample was incubated in the serum-free medium at 27° C. for 48 hours, followed by further incubation that extended 4 to 7 days until confluent cells were obtained on the serum-free medium with the additional 400 μg/mL antibiotic zeocin (Invitrogen Corporation). As a result, HBsAg-streptag particles were obtained.

The sample was centrifuged at 1500×g for 5 min, and the supernatant was collected. The HBsAg-streptag particles in the medium were measured for the presence or absence of expression, using the IMx kit (Dainabot Co. Ltd.). The result confirmed the expression of HBsAg-streptag particles. The HBsAg-streptag particles obtained from the supernatant were separated by SDS-PAGE and analyzed by Western blotting using an anti-S antibody (prepared by the inventors), followed by enzyme immunoassay IMx. The HBsAg-streptag particles fused with the streptag had a molecular weight of about 42 kDa.

1 L of the supernatant was concentrated with an ultrafiltration unit (filter UK-200, the product of Advantec, exclusion molecular weight 200 K), and purified through an anion exchange column (DEAE-Toyopearl 650 M, Toyo Soda). As a result, about 1 mg of pure uniform HBsAg-streptag particles were obtained.

Example C-3

Preparation of HBsAg-Streptag Particles in Animal Cells

Figure 5:
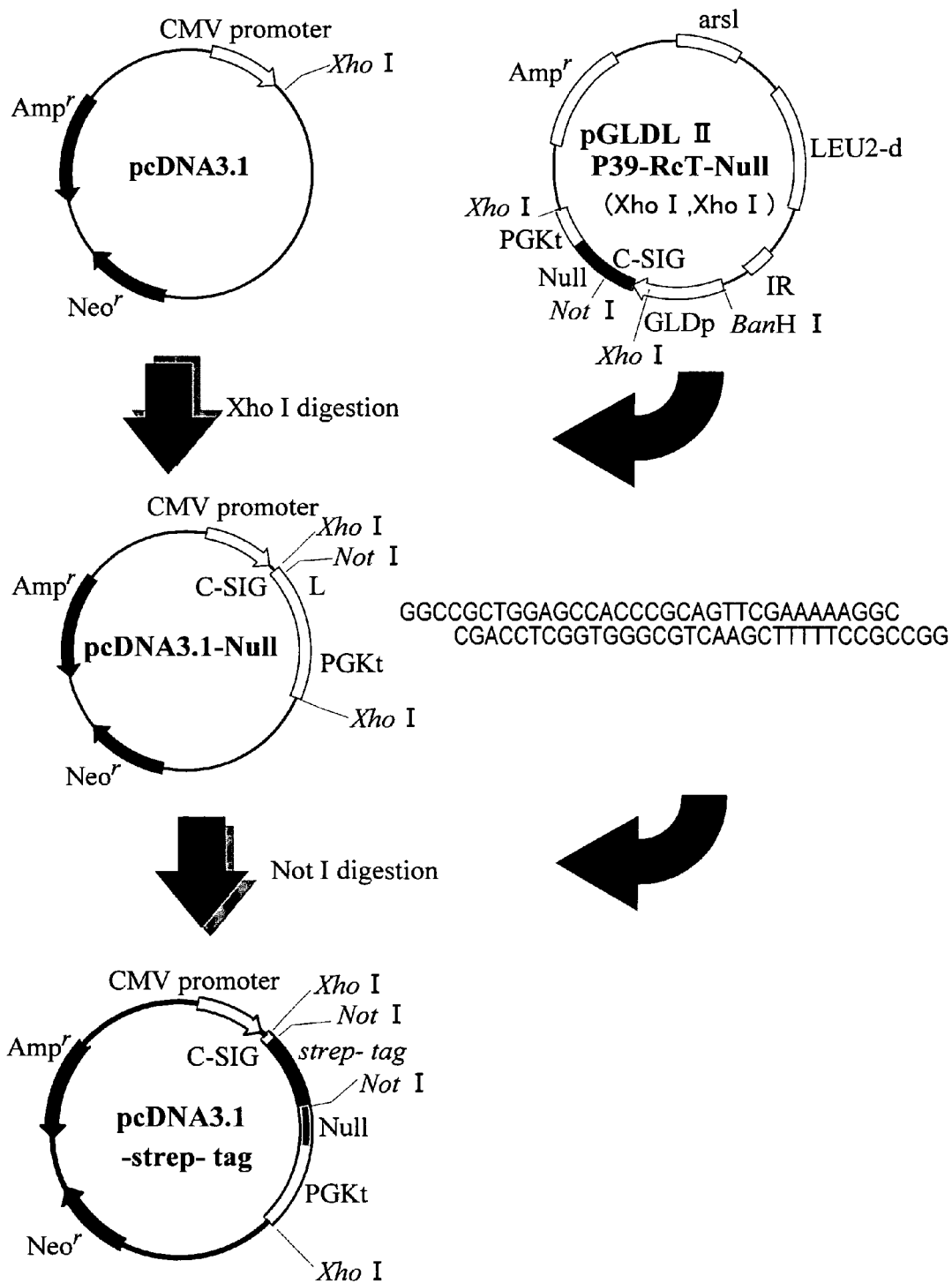
FIG. 5 is a diagram showing steps of constructing a plasmid used for preparation of HBsAg-streptag particles with animal cells, as described in Examples of the present invention.

As shown in FIG. 5, restriction enzyme XhoI was used to cleave the pGLDLIIP39-RcT-Null plasmid at the Xho site, so as to obtain fragments containing the Null region with a terminator (PGKt). After digesting pcDNA3.1 (Invitrogen Corporation) with restriction enzyme XhoI, the fragments were inserted into the pcDNA3.1 to prepare a pcDNA3.1-Null plasmid.

Thereafter, as in Example C-1, synthetic oligonucleotides (oligonucleotide of SEQ ID NO: 5, and oligonucleotide of SEQ ID NO: 6 complementary to SEQ ID NO: 5) that encodes a streptag gene were annealed and inserted into the pcDNA3.1-Null plasmid digested with NotI. As a result, a pcDNA3.1-streptag plasmid was prepared that included a coding region for the streptag.

The pcDNA3.1-streptag plasmid so obtained was then transferred into COS7 cells derived from the monkey kidney, using the gene transfer device gene pulser (Bio-Rad Laboratories, Inc.). After the transfer, the sample was incubated overnight in a Dulbecco-modified medium containing 10% fetal bovine serum. After further incubation in a serum-free medium CHO-SFMII (Gibco-BRL) for a week, the medium was purified to obtain HBsAg-streptag particles.

As in Example C-2, the HBsAg-streptag particles obtained from the supernatant were separated by SDS-PAGE and analyzed by Western blotting using an anti-S antibody, followed by enzyme immunoassay IMx. The HBsAg-streptag particles fused with the streptag had a molecular weight of about 42 kDa. The measured values of IMx were 8.81 (against cut-off value) for the wild-type HBsAg L particles expressed with the pcDNA3.1 vector, 3.47 for the HBsAg Null particles, and 2.41 for the HBsAg-streptag particles. All of these values can be considered to be sufficient.

Example C-4

Method of Displaying an Antibody on the HBsAg-Streptag Particles having a Streptag The foregoing Examples C-1 through C-3 prepared HBsAg-streptag particles with a streptag. The streptag specifically binds to streptavidin, which in turn specifically binds to biotin. By taking advantage of these specific bindings, the HBsAg-streptag particles are first bound to streptavidin, which is then ligated to a biotin-modified antibody. The result is HBsAg-streptag particles with the antibodies arrayed on the particle surface (such HBsAg-streptag particles will be referred to as "HBsAg-streptag-Ab particles" hereinafter).

Specifically, the anti-human EGFR mouse monoclonal antibody 7G7B6 (purified), which is an antibody against the human epidermal growth factor receptor (EGFR), is used as an antibody, and the NHS-biotin (EZ-Link® NHS-Biotin, the product of Pierce Biotechnology, Inc.) was tagged according to the protocol described in the instructions of the Pierce product. The purified HBsAg-streptag particles were then ligated to the avidin protein (ImmunoPure Avidin, the product of Pierce Biotechnology, Inc.) by mixing the two in PBS at a molar ratio of 2:1 and at ordinary temperature for 30 min (molar calculation was made on a molecular basis). Thereafter, the biotin-tagged anti-human EGFR mouse monoclonal antibody was allowed to react with an equimolar amount of HBsAg-streptag particles bearing the avidin protein. The reaction was carried out in PBS at ordinary temperature for 30 min. The result was HBsAg-streptag-Ab particles bearing the antibodies on the particle surface.

Example C-5

Transfer of Genes into the HBsAg-Streptag-Ab Particles

According to the method described in International Publication WO01/64930, the HBsAg-streptag-Ab particles were mixed with a green fluorescent protein expression plasmid (pEGFP-F (Clontech)), and the pEGFP-F was sealed in the HBsAg-streptag-Ab particles by an electroporation method. The result was HBsAg-streptag-Ab particles that had anti-human EGFR antibodies on the particle surface and encapsulated GFP expression plasmid inside the particles.

Next, there were prepared human squamous cell carcinoma-derived cells A431 (JCRB9009), along with human hepatic cancer-derived cells NUE and human colon cancer-derived cells WiDr as negative controls. The A431 and negative controls (NUE, WiDr) were each placed on a 3.5 cm glass-bottomed Petri dish, and incubated for 4 days with 1 μg of HBsAg-streptag-Ab particles encapsulating the GFP expression vector plasmid. GFP expression in the cells of the respective samples were observed with a confocal laser fluorescence microscope.

The observation found GFP fluorescence in A431 but not in the negative controls (NUE cells, WiDr).

Thus, with the HBsAg-streptag-Ab particles that had anti-human EGFR antibodies on the particle surface and encapsulated GFP expression plasmid inside the particles, the experiment showed that the transfer and expression of the gene was very specific and efficient in the A431 cells on the cultured cell level. The experiment therefore suggests that the HBsAg-streptag-Ab particles encapsulating a substance to be transferred into a cell for treating a disease have a potential use in the effective treatment of specific diseased cells or tissues.

Example D

Preparation of Antibody-Displaying HBsAg-ZZ Particles Using a ZZ Tag

Example D-1

Preparation of HBsAg-ZZ Particles in Yeast Cells

Figure 6:
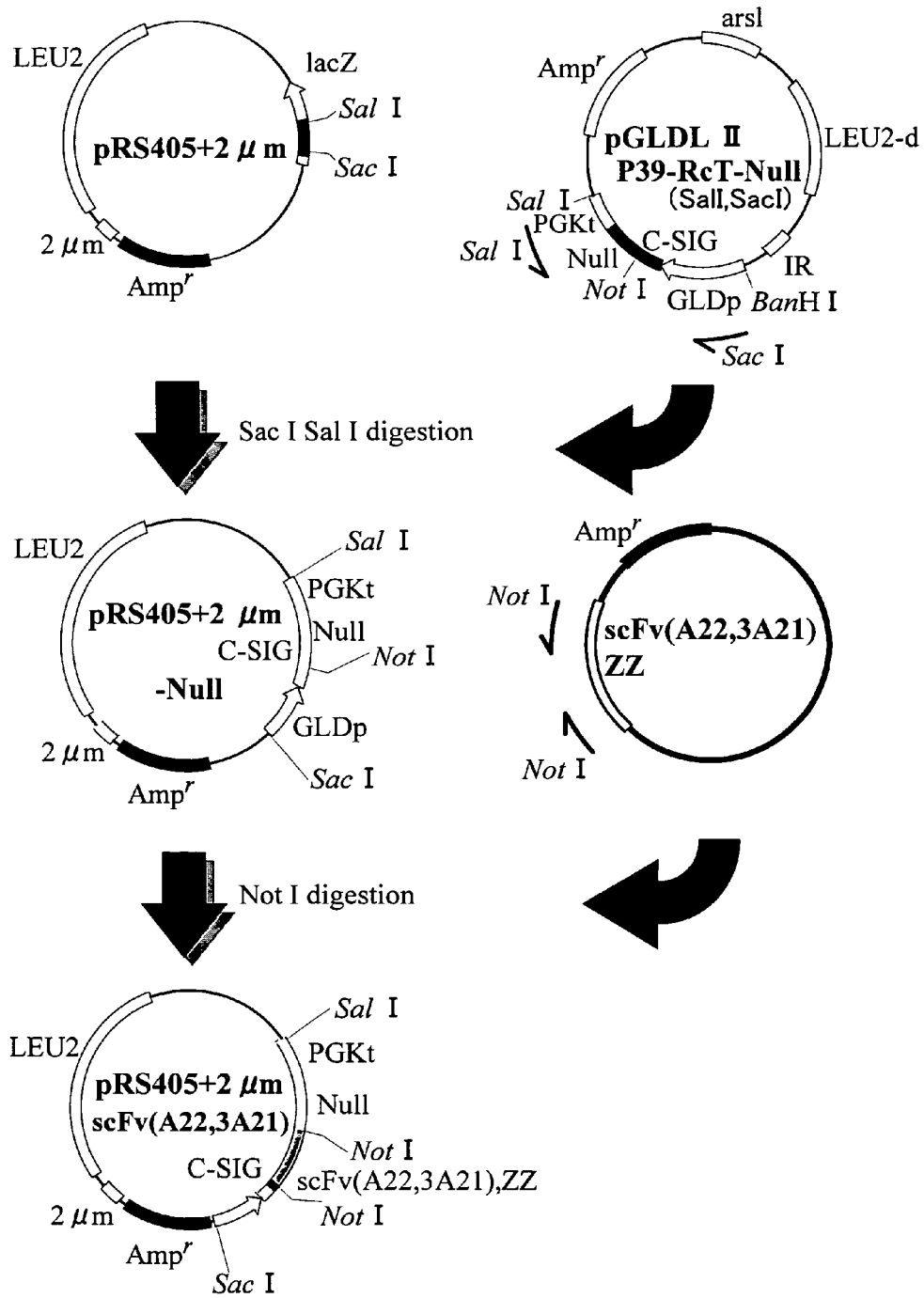
FIG. 6 is a diagram showing steps of constructing a plasmid used for preparation of HBsAg-ZZ tag particles with yeasts, as described in Examples of the present invention.

As in Example C-1, a pRS405+2 μm-Null plasmid was prepared as shown in FIG. 6.

Using NotI site-containing oligonucleotides of SEQ ID NOs: 9 and 10 as PCR primers, PCR was run for a plasmid that contained a coding region for a ZZ tag (indicated by "ZZ" in the figure; hereinafter referred to as "ZZ region") (prepared by inserting a ZZ region based on a Protein A gene derived from Staphylococcus aureus). The PCR amplified regions including the ZZ region. The ZZ tag is defined as an amino acid sequence with the ability to bind to the Fc region of immunoglobulin G, wherein the amino acid sequence has the following two repeating units from the N-terminus (ZZ tag sequence (SEQ ID NO: 29)):

```
VDNKFNKEQQNAFYEILHLPNLNEEQRNAFIQSLKDDPSQSANLLA
EAKKLNDAQAPK

VDNKFNKEQQNAFYEILHLPNLNEEQRNAFIQSLKDDPSQSANLLA
EAKKLNDAQAPK
```

The pRS405+2 μm-Null plasmid was then digested with restriction enzyme NotI, and the amplified fragments were inserted in the cleaved plasmid to prepare a pRS405+2 μm-ZZ plasmid.

As in Example A, the plasmid gene pRS405+2 μm-ZZ was used to transform the yeast S. cerevisiae AH22R$^-$ by a spheroplast method. The resulting transformants were incubated in medium High-Pi (3 ml) at 30° C. for 3 days, and subsequently in medium 8S5N-P400 (3 ml) at 30° C. for another 3 days, so as to prepare HBsAg particles displaying a ZZ tag.

The pRS405+2 μm-ZZ plasmid so obtained was used to transform the yeast (Saccharomyces cerevisiae AH22R$^-$ strain). The resulting transformants were incubated, and the cultured cells were purified according to the method described in Example B to obtain modified HBsAg particles (particles obtained by expressing the ZZ tag fused with the HBsAg L protein lacking the human hepatocyte recognition site). The efficiency of particle expression was very high, producing about 20 mg of pure HBsAg-ZZ tag particles from the yeasts derived from 1.0 L medium.

Figure 7:
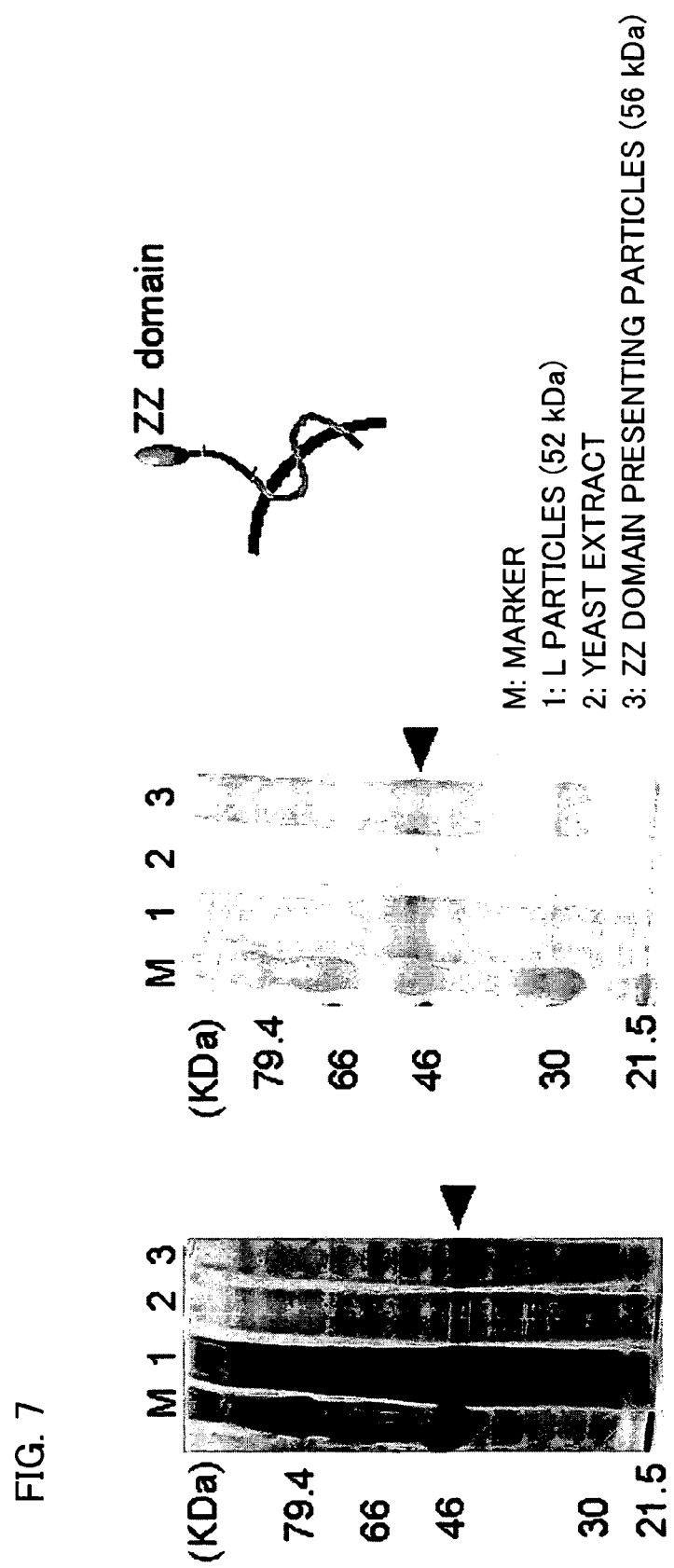
FIG. 7 is a diagram representing results of SDS-PAGE and Western blotting performed on the HBsAg-ZZ tag particles obtained with yeasts.

The HBsAg-ZZ tag particles obtained from the supernatant were separated by SDS-PAGE, and analyzed by Western blotting using an anti-S antibody, followed by enzyme immunoassay IMx. FIG. 7 shows the results of SDS-PAGE and Western blotting. The measured values of IMx were 49.43 (against cut-off value, ×100 diluted) for the wild-type HBsAg L particles expressed with the pRS405+2 μm vector, 21.87 for the HBsAg Null particles, and 253.64 for the HBsAg-ZZ tag particles. All of these values can be considered to be sufficient. The HBsAg-ZZ tag particles with the ZZ tag had a molecular weight of about 56 kDa.

Example D-2

Preparation of HBsAg-ZZ Tag Particles in Insect Cells in Serum-Free Medium

Figure 8:
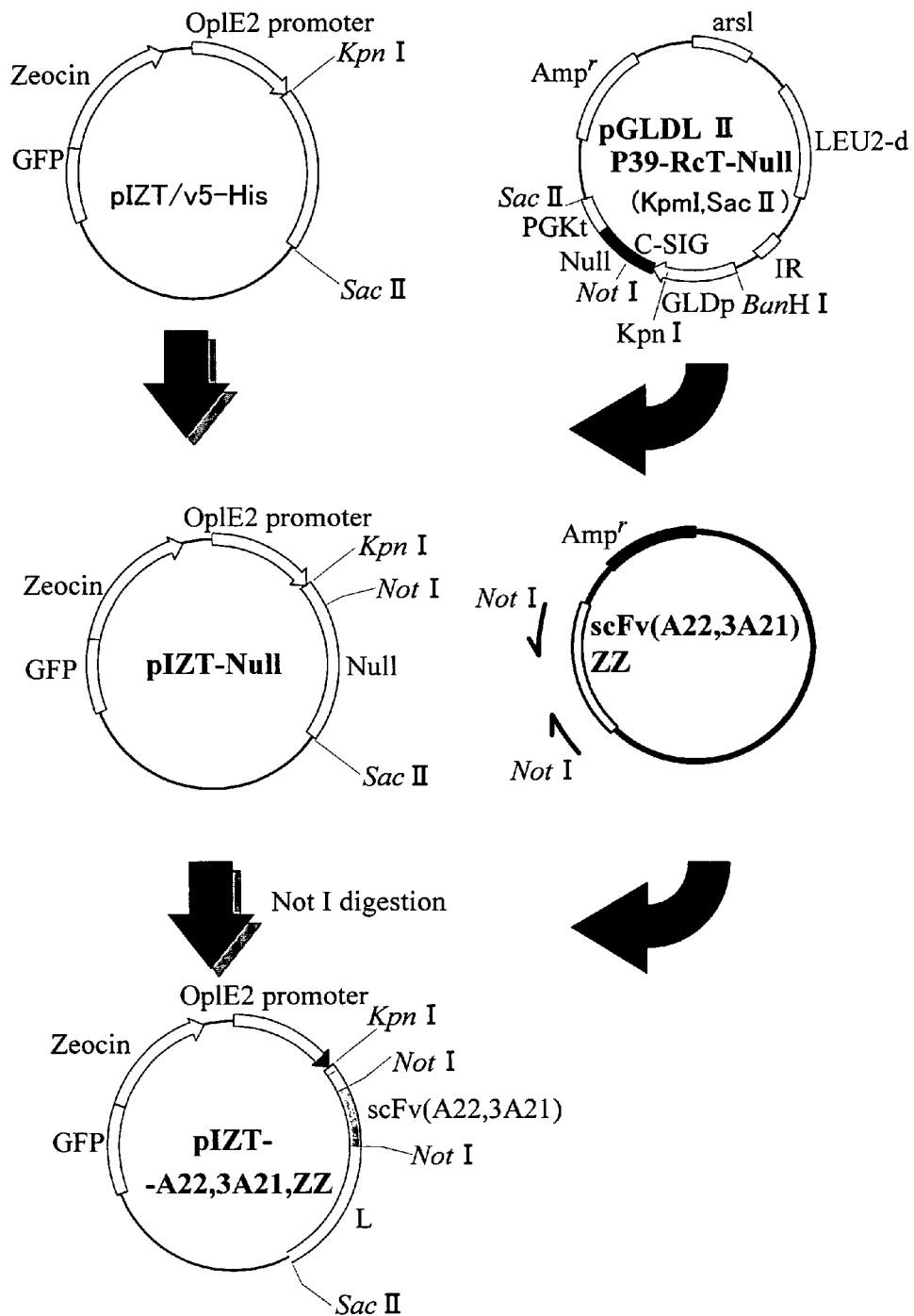
FIG. 8 is a diagram showing steps of constructing a plasmid used for preparation of HBsAg-ZZ tag particles (or HBsAg-scFv particles displaying single chain antibody A22 or 3A21) with insect cells, as described in Examples of the present invention.

As shown in FIG. 8, a pIZT-Null plasmid was obtained according to the method described in Example C-2.

A region including the ZZ region was inserted in the pIZT-Null plasmid according to the method of Example D-1, so as to prepare a pIZT-ZZ plasmid.

The pIZT-ZZ plasmid so obtained was inserted in insect cells, and HBsAg-ZZ tag particles were expressed therein according to the method of Example C-2.

After incubating the insect cells, the supernatant was collected. The HBsAg-ZZ tag particles obtained from the supernatant were separated by the SDS-PAGE, and analyzed by Western blotting using an anti-S antibody (prepared by the inventors, mouse polyclonal antibody). The result showed that the HBsAg-ZZ tag particles displaying the ZZ tag had a molecular weight of about 56 kDa.

The amount of HBsAg-ZZ tag particles obtained from 1 L supernatant was about 1 mg according to the method of Example C-2.

Example D-3

Preparation of HBsAg-ZZ Tag Particles in Animal Cells

Figure 9:
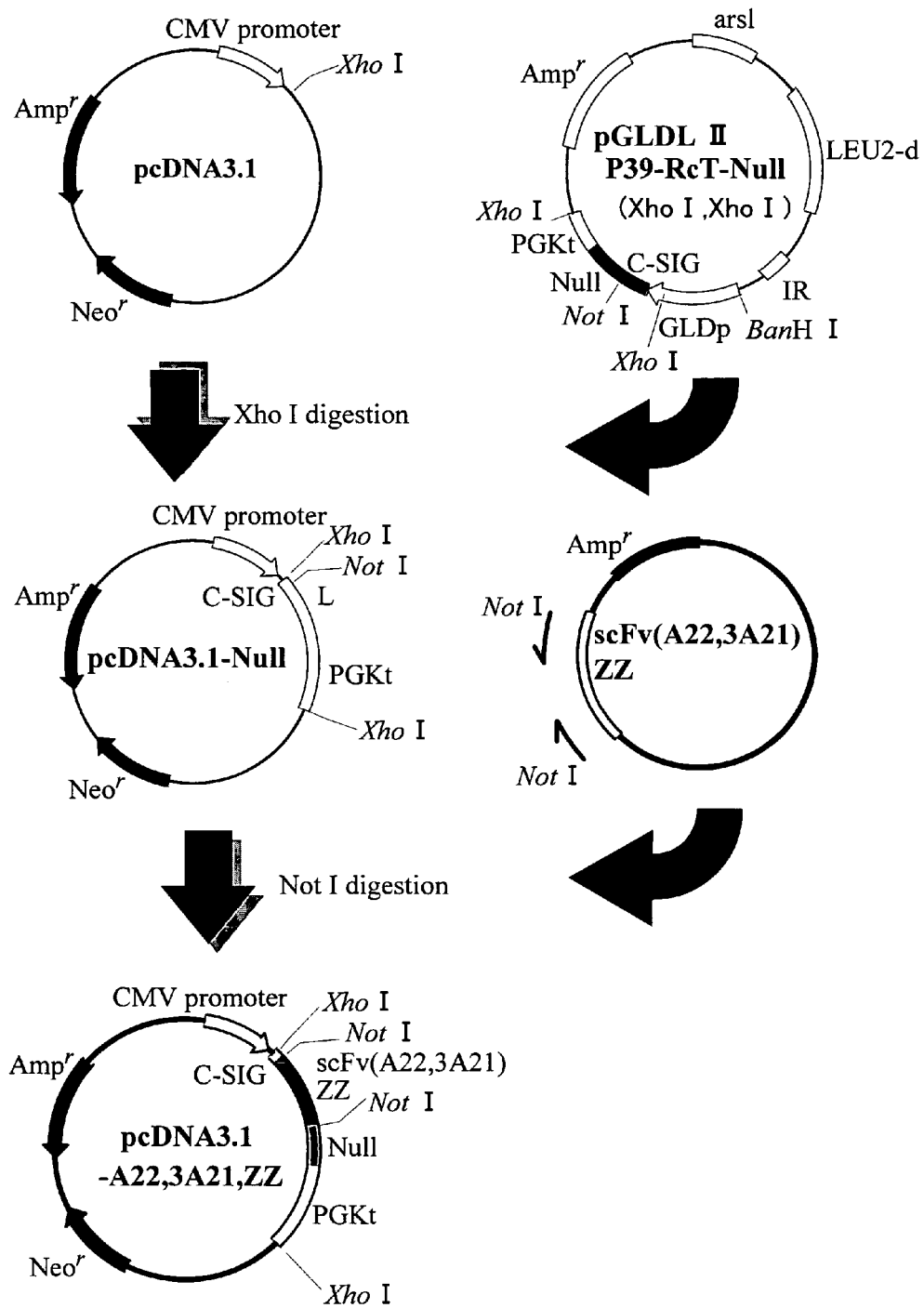
FIG. 9 is a diagram showing steps of constructing a plasmid used for preparation of HBsAg-ZZ tag particles (or HBsAg-scFv particles displaying single chain antibody A22 or 3A21) with animal cells, as described in Examples of the present invention.

As shown in FIG. 9, a pcDNA3.1-Null plasmid was obtained according to the method described in Example C-3.

Then, a region including the ZZ region was inserted in the pcDNA3.1-Null plasmid according to the method of Example D-1, so as to prepare a pcDNA3.1-ZZ plasmid.

The pcDNA3.1-ZZ plasmid so obtained was inserted in COS7 cells, and HBsAg-ZZ tag particles were expressed therein according to the method of Example C-3.

After incubating the COS7 cells, the supernatant was collected. The HBsAg-ZZ tag particles obtained from the supernatant were separated by the SDS-PAGE, and analyzed by Western blotting using an anti-S antibody (prepared by the inventors, mouse polyclonal antibody), followed by enzyme immunoassay IMx. The measured values of IMx were 8.81 (against cut-off value) for the wild-type HBsAg L particles expressed with the pcDNA3.1 vector, 3.47 for the HBsAg Null particles, and 2.41 for the HBsAg-ZZ tag particles. All of these values can be considered to be sufficient. The HBsAg-ZZ tag particles with the ZZ tag had a molecular weight of about 56 kDa.

Example D-4

Method of Displaying an Antibody on the HBsAg-ZZ Tag Particles

The ZZ tag has strong affinity to the Fc portion of the antibody molecule. For example, the ZZ tag can specifically bind to the cancer-specific mouse monoclonal antibody 7G7B6 against the human EGF receptor (EGFR). Other examples of antibodies specific to the ZZ tag include the mouse monoclonal antibody 528 against the human IL-2 receptor (Tac antigen), and the colon cancer-specific mouse monoclonal antibody ST-421 against the human colon cancer. By binding the HBsAg-ZZ tag particles to these antibodies, HBsAg-ZZ tag particles were prepared that had the antibodies arrayed on the particle surface (hereinafter, such HBsAg-ZZ tag particles will be referred to as "HBsAg-ZZ tag-Ab particles").

Specifically, the HBsAg-ZZ tag particles were mixed with an equimolar amount of anti-human EGFR mouse monoclonal antibody 7G7B6 (purified) (molar calculation was made on a molecular basis), and the mixture was allowed to react for one hour in PBS. The result was HBsAg-ZZ tag-Ab particles with the antibodies displayed on the particle surface.

Example D-5

Transfer of Genes into the HBsAg-ZZ Tag-Ab Particles

According to the method disclosed in International Publication WO01/64930, the HBsAg-ZZ tag-Ab particles were mixed with a green fluorescent protein expression plasmid (pEGFP-F (Clontech)), and the pEGFP-F was sealed in the HBsAg-ZZ tag-Ab particles by an electroporation method. The result was HBsAg-ZZ tag-Ab particles that had anti-human EGFR antibodies on the particle surface and encapsulated GFP expression plasmid inside the particles.

Next, as in Example C-5, there were prepared human squamous cell carcinoma-derived cells A431, along with human hepatic cancer-derived cells NUE and HuH-7 (JCRB0403) and human colon cancer-derived cells WiDr (ATCC CCL-218) as negative controls. The A431 and negative controls (NUE, HuH-7, WiDr) were each placed on a 3.5 cm glass-bottomed Petri dish, and incubated for 4 days with 1 µg of HBsAg-ZZtag-Ab-GFP particles encapsulating the GFP expression vector plasmid. GFP expression in the cells of the respective samples were observed with a confocal laser fluorescence microscope.

The observation found GFP fluorescence in A431 but not in the other cells (e.g., NUE cells).

Thus, with the HBsAg-ZZ tag-Ab particles that had anti-human EGFR antibodies on the particle surface and encapsulated GFP expression plasmid inside the particles, the experiment showed that the transfer and expression of the gene was very specific and efficient in the A431 cells on the cultured cell level.

Meanwhile, human tumor strains (A431, HuH-7, WiDr) were injected by hypodermic injection into nude mice (lineage: BALB/c, nu/nu, microbiological quality: SPF, male, 5 weeks of age). The injection was made in the bilateral dorsal area of the mouse with $1 \times 10^7$ cells for each strain. In order to obtain a carrier mice, the mice were grown for 2 to 4 weeks until the transplanted tumor developed into a solid cancer tumor of about 2 cm diameter.

The HBsAg-ZZ tag-Ab particles encapsulating the GFP expression plasmid were administered into the abdomen of each mouse with a 26 G syringe. The mouse was killed 4 days after the administration, and the tumor area was removed along with various organs including liver, spleen, kidney, and intestines. The tissues were fixed and embedded using the GFP resin embedding kit (Technovit 7100).

Specifically, the samples were fixed by immersing them in 4% neutralized formaldehyde, and were dried in 70% EtOH at room temperature for 2 hours, 96% EtOH at room temperature for 2 hours, and 100% EtOH at room temperature for one hour. Pre-fixation was carried out for 2 hours at room temperature in a mixture containing equal amounts of 100% EtOH and Technovit 7100. The samples were further immersed in Technovit 7100 for no longer than 24 hours at room temperature. Out of the solution, the samples were allowed to stand for one hour at room temperature and for another one hour at 37° C. for polymerization.

According to ordinary method, the sample were sliced and stained with hematoxin-eosin (common method of tissue staining). GFP fluorescence of each slice was observed with a fluorescent microscope. The result showed that human squamous cell carcinoma-derived cells A431 had GFP fluorescence. No fluorescence was observed in the organs removed from the same mouse, including liver, spleen, kidney, and intestines. On the other hand, in carrier mice that have incorporated cells derived from other types of human cancer (HuH-7, WiDr), no GFP fluorescence was observed in the tumor area, or in the liver, spleen, kidney, or intestines. Fluorescence was not observed either in carrier mice to which the HBsAg-ZZ tag was not administered.

Thus, with the HBsAg-ZZ tag-Ab particles that had anti-human EGFR antibodies on the particle surface and encapsulated GFP expression plasmid inside the particles, the experiment showed that the transfer and expression of the gene was very specific and efficient in the A431 cells on the laboratory animal level.

Example D-6

Effectiveness of Treatment using the HBsAg-ZZ Tag-Ab Particles

In order to produce the HBsAg-ZZ tag-Ab particles as a drug of the present invention encapsulating HSV1tk gene, a cancer-treating thymidine kinase derived from simple herpes virus (HSV1tk) was sealed in the HBsAg-ZZ tag-Ab particles that were prepared in yeasts according to the described method.

The cancer cells that have incorporated the HSV1tk gene become ganciclovir (GCV) sensitive when they express the gene. Administration of ganciclovir therefore kills off the cancer cells by the strong effect it exhibits on the cancer cells. This is one reason the HSV1tk gene has been widely used in the gene therapy of cancer.

In this Example, the HSV1tk gene was sealed in the HBsAg-ZZ tag-Ab particles using a vector pGT65-hIFN-α (the product of Invitrogen Corporation) that expresses the HSV1tk gene. The HBsAg-ZZ tag-Ab particles encapsulating the HSV1tk gene were obtained by transferring the expression vector into the HBsAg-ZZ tag-Ab particles by an electroporation method. Specifically, 10 μg of expression vector was transferred into 50 μg of L protein particles in the HBsAg-ZZ tag-Ab particles. The vector was transferred using a PBS buffer, and the electroporation was carried out with a 4 mm cuvette under 220 V and 950 μF.

As the laboratory animal, the present Example used nude rats purchased from CLEA Japan, Inc. (lineage: F344/NJcl-rnu/rnu, female). By hypodermic injection, human squamous cell carcinoma-derived cells A431 were transplanted into the nude rats, along with the human colon cancer-derived cells WiDr as a negative control. The injection was made in the bilateral dorsal area of the rats with $1 \times 10^7$ cells for each cell type. The rats were grown for about 3 weeks until the grafted tumor developed into a solid cancer tumor of about 2 to 3 cm diameter.

Figure 10:
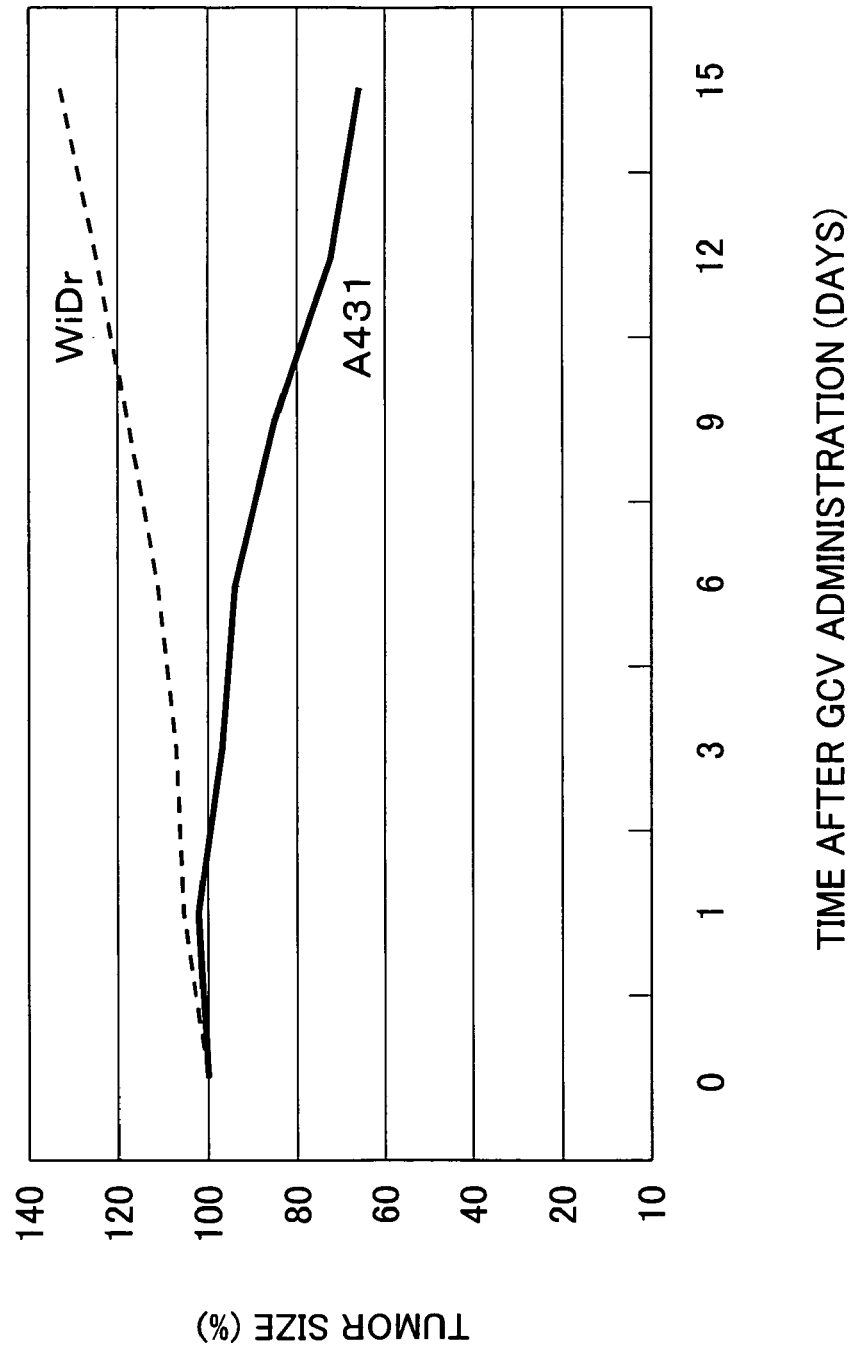
FIG. 10 is a graph showing a result of treatment on laboratory animals using the HBsAg-ZZ tag particles as a drug of the present invention.

10 μg of HBsAg-ZZ tag-Ab particles encapsulating the HSV1tk gene were administered to each nude rat through the tail vein (intravenous injection). Starting from 5 days after the intravenous injection, ganciclovir (GCV) was administered to each rat with the dose of 50 mg/kg/day, using an osmotic pump (alzet osmotic pump; Cat No. 2ML2). Here, the GCV was administered to the back of each nude rat subcutaneously. The GCV was administered for no longer than 14 days. After the administration, the state (size) of the tumor tissue of the nude rats was observed over time. Specifically, the major axis and minor axis of the tumor part were measured with a gauge, and a tumor volume was approximated (major axis×minor axis×minor axis/2). The rats were measured in triplet. The results are shown in FIG. 10 and FIG. 27.

Thus, with the HBsAg-ZZ tag-Ab particles that had anti-human EGFR antibodies on the particle surface and encapsulated the HSV1tk gene inside the particles, the experiment showed that the transfer and expression of the gene was very specific and efficient in the A431 cells and therefore highly effective in cancer treatment on the laboratory animal level.

Example E

Preparation of HBsAg-scFv Particles Displaying a Single Chain Antibody

Example E-1

Preparation of HBsAg-scFv Particles in Yeast Cells

A region of including a coding region for antibody A22 or 3A21 was amplified by PCR, where the antibody A22 is a single chain anti-human serum albumin antibody derived from mice, and the antibody 3A21 is a single chain anti-human RNase antibody derived from mice. PCR was performed according to the procedure of Example D-1, except that a different plasmid and different PCR primers were used.

As the plasmid that includes a ZZ region, the present Example used either a plasmid that includes a coding region for the antibody A22 (generous gift of TOTO LTD.), or a plasmid that includes a coding region for the antibody 3A21. (prepared according to the method described in Mol Immunol. 1997 August-September; 34(12-13): 887-90 Katakura Y, Kumamoto T, Iwai Y, Kurokawa Y, Omasa T, Suga K., and Mol Immunol 1997 July; 34(10): 731-4 Katakura Y, Kumamoto T, Iwai Y, Kurokawa Y, Omasa T, Suga K.) As the PCR primers, the present Example used either oligonucleotides of SEQ ID NOs: 11 and 12 (in the case of A22), or oligonucleotides of SEQ ID NOs: 13 and 14 (in the case of 3A21), where each oligonucleotide had a NotI site. The single chain antibody (scFv) is a pseudo antibody molecule that has been restructured to have the antigen recognition site only on a single chain polypeptide, rather than the normal double chain polypeptide.

The amplified fragments obtained by the PCR were inserted in the pRS405+2 μm-Null plasmid to prepare pRS405+2 μm-A22 plasmid or pRS405+2 μm-3A21 plasmid. The pRS405+2 μm-A22 or pRS405+2 μm-3A21 plasmid was transferred into yeasts and expressed therein. The result was particles whose particle surface had single chain antibody A22 or 3A21 expressed with the HBsAg L protein fused with the antibody (such particles will be referred to as HBsAg-scFv particles hereinafter).

Figure 11:
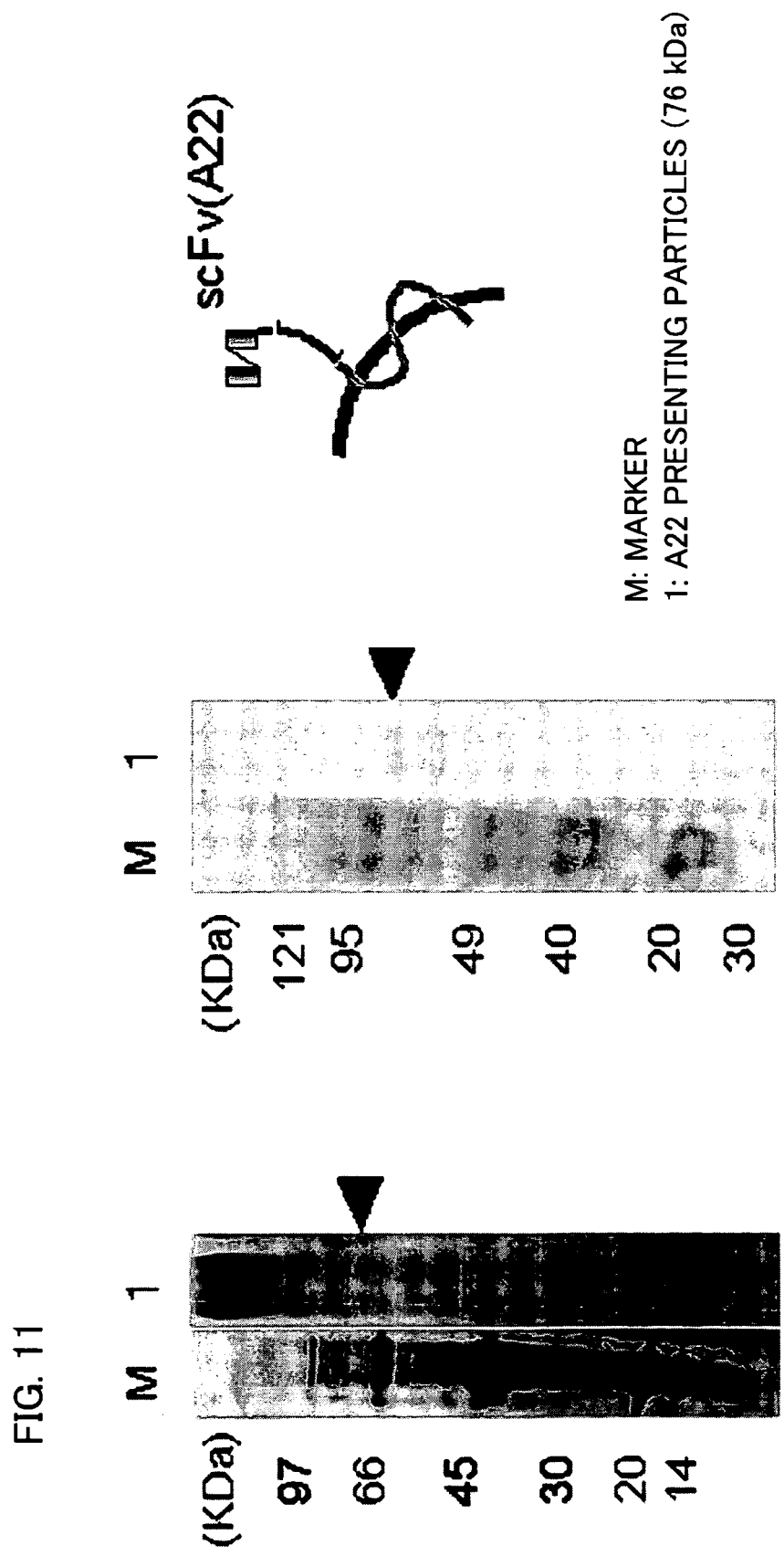
FIG. 11 is a diagram representing results of SDS-PAGE and Western blotting performed on the HBsAg-scFv particles.

After incubating the yeasts, the supernatant was collected. The HBsAg-scFv particles obtained from the supernatant were separated by SDS-PAGE, and analyzed by Western blotting using an anti-S antibody, followed by enzyme immunoassay IMx. FIG. 11 shows the results of SDS-PAGE and Western blotting. The measured values of IMx were 49.43 (against cut-off value, ×100 diluted) for the wild-type HBsAg L particles expressed with the pRS405+2 μm vector, 21.87 for the HBsAg Null particles, 2.41 for the HBsAg-scFv particles displaying A22, and 4.02 for the HBsAg-scFv particles displaying 3A21. All of these values can be considered to be sufficient. The HBsAg-scFv particles with antibody A22 had a molecular weight of about 76 kDa. The result was the same for the HBsAg-scFv particles with antibody 3A21. By the method of Example C-2, about 200 μg of pure HBsAg-scFv particles were obtained from the yeasts derived from 1.0 L medium.

Example E-2

Preparation of HBsAg-scFv Particles in Insect Cells in Serum-Free Medium

As shown in FIG. 8, a region of including a coding region for antibody A22 or 3A21 was amplified by PCR, where the antibody A22 is a single chain anti-human serum albumin antibody derived from mice, and the antibody 3A21 is a single chain anti-human RNase antibody derived from mice. PCR was performed according to the procedure of Example D-2, except that a different plasmid and different PCR primers were used. As the plasmid that includes a ZZ region, a plasmid that includes a coding region for the antibody A22 or 3A21 was used. As the PCR primers, the present Example used either oligonucleotides of SEQ ID NOs: 11 and 12 (in the case of A22), or oligonucleotides of SEQ ID NOs: 13 and 14 (in the case of 3A21), where each oligonucleotide had a NotI site.

The amplified fragments obtained by the PCR were inserted in the pRS405+2 μm-Null plasmid to prepare pIZT-A22 plasmid or pIZT-3A21 plasmid. The pIZT-A22 or pIZT-3A21 plasmid was transferred into insect cells and expressed therein. The result was HBsAg-scFv particles displaying the single chain antibody A22 or 3A21.

After incubating the insect cells, the supernatant was collected. The HBsAg-scFv particles obtained from the supernatant were separated by SDS-PAGE, and analyzed by Western blotting using an anti-S antibody. The HBsAg-scFv particles with antibody A22 had a molecular weight of about 76 kDa. The result was the same for the HBsAg-scFv particles with antibody 3A21.

By the method of Example C-2, about 1 mg of pure HBsAg-scFv particles were obtained from 1.0 L supernatant.

Example E-3

Preparation of HBsAg-scFv Particles in Animal Cells

As shown in FIG. 9, a region including a coding region for antibody A22 or 3A21 was amplified by PCR, where the antibody A22 is a single chain anti-human serum albumin antibody derived from mice, and the antibody 3A21 is a single chain anti-human RNase antibody derived from mice. PCR was performed according to the procedure of Example D-3, except that a different plasmid and different PCR primers were used. As the plasmid that includes a ZZ region, a plasmid that includes a coding region for the antibody A22 or 3A21 was used. As the PCR primers, the present Example used either oligonucleotides of SEQ ID NOs: 11 and 12 (in the case of A22), or oligonucleotides of SEQ ID NOs: 13 and 14 (in the case of 3A21), where each oligonucleotide had a NotI site.

The amplified fragments obtained by the PCR were inserted in the pcDNA3.1 plasmid to prepare pcDNA3.1-A22 plasmid or pcDNA3.1-3A21 plasmid. The pcDNA3.1-A22 or pcDNA3.1-3A21 plasmid was transferred into animal cells and expressed therein. The result was HBsAg-scFv particles displaying the single chain antibody A22 or 3A21.

After incubating the COS7 cells, the supernatant was collected. The HBsAg-scFv particles obtained from the supernatant were separated by SDS-PAGE, and analyzed by Western blotting using an anti-S antibody. The result showed that HBsAg-scFv particles with antibody A22 had a molecular weight of about 76 kDa. The result was the same for the HBsAg-scFv particles with antibody 3A21.

Example E-4

Transfer of Genes into the HBsAg-scFv Particles

The HBsAg-scFv particles so prepared were fixed on 96-well plates, wherein human serum albumin was used for the HBsAg-scFv particles that had antibody A22, and human RNase 1 was used for the HBsAg-scFv particles that had 3A21 antibody. Binding factors of the respective samples were measured by an ELISA. The amount of HBsAg-scFv particles that bound in the stationary phase was quantified using the HRP tag anti-HBsAg polyclonal antibody provided in the AUSZYME II of Dainabot Co. Ltd. The result showed that the HBsAg-scFv particles had binding factors of not more than 100 nM for A22, and not more than 50 nM for 3A21. The results are based on proteins building the HBsAg-scFv particles, not the HBsAg-scFv particles themselves. The binding factors in these ranges are sufficient for the HBsAg-scFv particles to serve as a carrier for delivering a drug or other substances to a specific site inside the body.

The experiment showed that the HBsAg-scFv particles displaying the antibody A22 or 3A21 on the particle surface were highly specific to the A431 cells.

Example F

By expressing various types of deletion HBsAg L proteins lacking amino acids in the pre-S region (pre-S1, pre-S2), which is the human hepatocyte recognition site of the HBsAg L protein, the present Example evaluated the level of expression and antigenicity in eukaryotic cells among different amino acid deletion regions.

Example F-1

Preparation of Deletion HBsAg L Protein Expression Genes

Deletion HBsAg L protein expression genes were prepared by PCR according to the method described below.

In order to obtain deletion HBsAg L proteins, there were prepared deletion HBsAg L protein expression genes that express 5 types of deletion HBsAg L proteins (a) to (e) below in which part of the pre-S regions (pre-S1 region, pre-S2 region) has been deleted. Specifically, the deletion HBsAg L proteins prepared in this Example are (a) a protein lacking N-terminal amino acids 21 to 153 in the pre-S region ($\Delta$21-153 in FIG. 12; the same notation is used below), (b) a protein lacking N-terminal amino acids 33 to 153 in the pre-S region ($\Delta$33-153), (c) a protein lacking N-terminal amino acids 50 to 153 in the pre-S region ($\Delta$50-153), (d) a protein lacking N-terminal amino acids 108 to 153 in the pre-S region ($\Delta$108-153), and (e) a protein lacking N-terminal amino acids 127 to 153 in the pre-S region ($\Delta$127-153).

In order to amplify deletion HBsAg L protein expression genes of the respective proteins (a) through (e), PCR was run for pB0477 (plasmid that has incorporated HbsAg L protein expression genes, prepared by the inventors) according to the described method. As the PCR primers, the oligonucleotides of SEQ ID NOs: 15 through 24 were used. The oligonucleotides of SEQ ID NOs: 15 and 16 were for amplifying the deletion HBsAg L protein (a), the oligonucleotides of SEQ ID NOs: 17 and 18 for (b), the oligonucleotides of SEQ ID NOs: 19 and 20 for (c), the oligonucleotides of SEQ ID NOs: 21 and 22 for (d), and the oligonucleotides of SEQ ID NOs: 23 and 24 for (e). Further, among the primers of SEQ ID NOs: 15 through 24, the odd-numbered ones are forward primers, and the even-numbered ones are reverse primers.

The reaction compositions of PCR are shown in FIG., 13: Pyrobest DNA polymerase (TaKaRa) (heat-resistant DNA polymerase) (0.5 μL), PCR buffer (5 μL×10), dNTP mixture (10 mM, 5 μL), template DNA (pB0477; plasmid that has incorporated the HbsAg L protein expression genes, prepared by the inventors) (5 μg/mL, 2 μL), and a primer set (SEQ ID NOs: 15 to 24) (1 μL each). The total volume was 50 μL with the addition of distilled water.

The PCR was run in 30 cycles as follows: 30 second denature at 98° C., 30 second denature at 98° C., 1 minute annealing at 55° C., and 30 minute synthesis at 68° C. The reaction was ended upon cooling to 4° C., as shown in FIG. 14. In order to cut the template DNA, the restriction enzyme DpnI (1OU) was added to the PCR product. After incubation at 37° C. for 1 hour, the resulting plasmid was used to transform E. coli JM109 strain. The plasmid was removed from the expression colonies, and its base sequence was confirmed.

Figure 15:
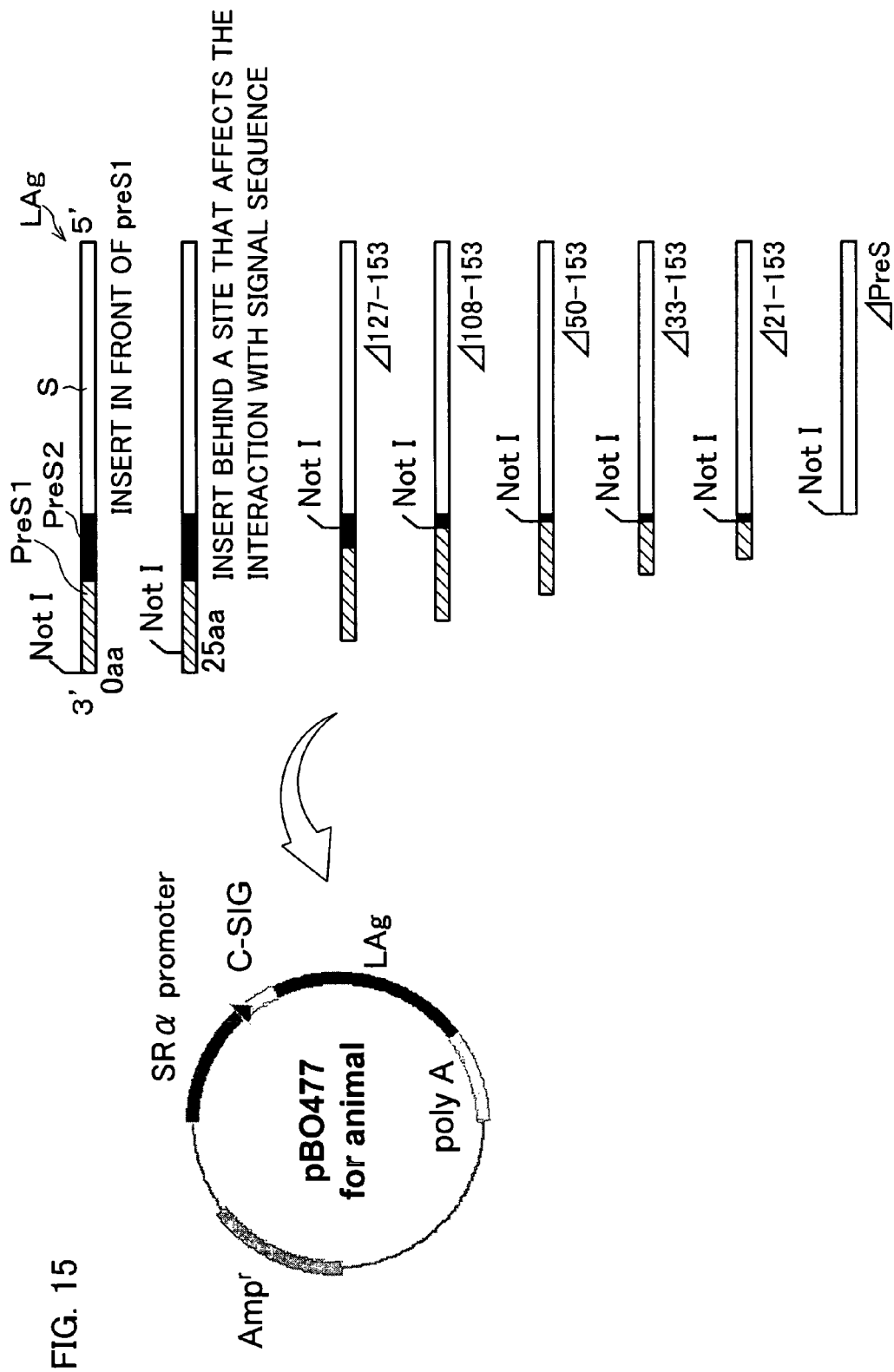
FIG. 15 is a schematic diagram illustrating deletion HBsAg protein expression genes and a plasmid into which the genes are transferred, as described in Examples of the present invention.

Thereafter, restriction enzyme NotI sites were introduced into the deletion HBsAg L protein. FIG. 15 schematically illustrates an expression gene that was prepared by introducing restriction enzyme NotI sites in the deletion HBsAg L protein expression gene. The schematic diagram of FIG. 15 also illustrates a plasmid that has incorporated such a gene. In FIG. 15, the restriction enzyme NotI sites are indicated by 0aa, 25aa, and ΔPreS, wherein 0aa is an insertion site at an end (5' end) of the deletion HBsAg L protein expression gene, 25aa is an insertion site at the 3' end of the first 25 amino acid residues from the 5' end, and ΔPreS is an insertion site at an end (5' end) of an S protein expression gene.

The deletion HBsAg L protein expression gene with the NotI sites was then inserted in a plasmid pB0477 (plasmid that has incorporated the HBsAg L protein expression gene, for expression in animal cells, prepared by the inventors) with XhoI, so as to obtain a recombinant HBsAg L protein expression gene.

Figure 12:
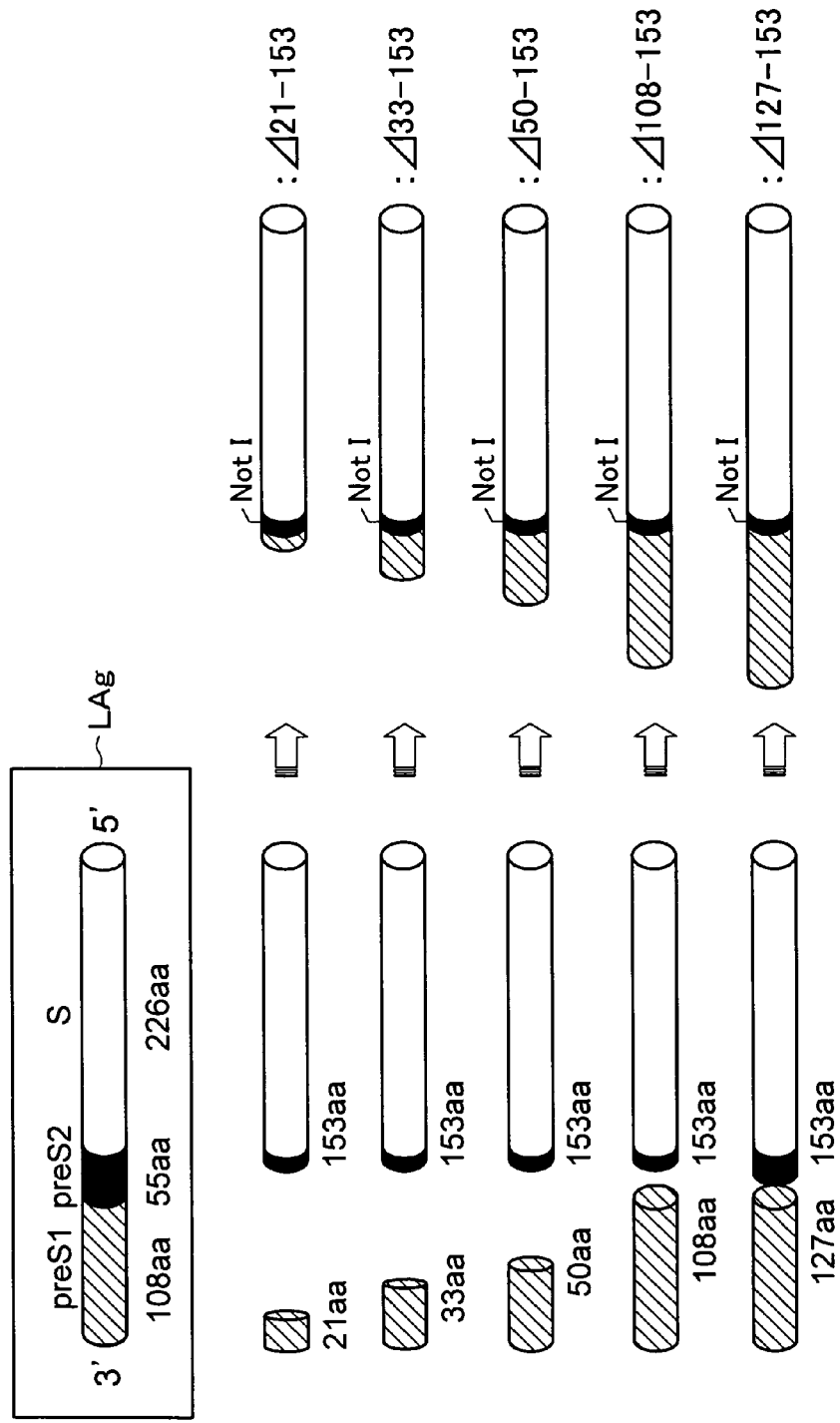
FIG. 12 is a schematic diagram showing deletion HBsAg protein expression genes, as described in Examples of the present invention.

Note that, in FIG. 15 and subsequent drawings, the notation A127-153 indicates that the HBsAg L protein expression gene shown in FIG. 12 lacks a gene that encodes amino acids 127 to 153, for example. (The same notation is used below.) Similarly, Δpre-S indicates that a gene that encodes all amino acids in the pre-S regions (pre-S1, pre-S2) is lacking.

Example F-2

Preparation of Deletion HBsAg L Protein in Animal Cells

The plasmid (2 μg) constructed in Example F-1 was used to transform Cos7 cells (3 to 8×10$^4$ cells) by electroporation (300 V, 950 μF). The resulting plasmid was allowed to stand at 37° C. for 4 days in the presence of 5% $CO_2$. The amount of mutant L particles (deletion HBsAg L protein) in the supernatant and cell extract was measured with an enzyme immunoassay device (Dainabot Co. Ltd.). The measurement was made based on the antigenicity of the mutant L particles. The supernatant used in the measurement had been diluted with the equal amount of PBS. The cell extract was obtained by causing the cells to lyse in a lysis buffer (20 mM Tris-HCl, 1 mM EDTA, 150 mM NaCl, 10 mM 2-mercaptoethanol, 1% (v/v) Triton X-100), followed by ×200 dilution of the lysate supernatant with PBS after centrifugation.

FIGS. 16(a) and 16(b) and FIG. 17 represent the results of measurement, showing the produced amount of mutant L particles (given in numerical values and graph). In these drawings, greater values of S/N and RATE indicate greater antigenicity. That is, samples Δ21-153, Δ33-153, and Δ50-153 produced good results, of which the deletion HBsAg L protein Δ50-153 was particularly desirable.

Figure 18:
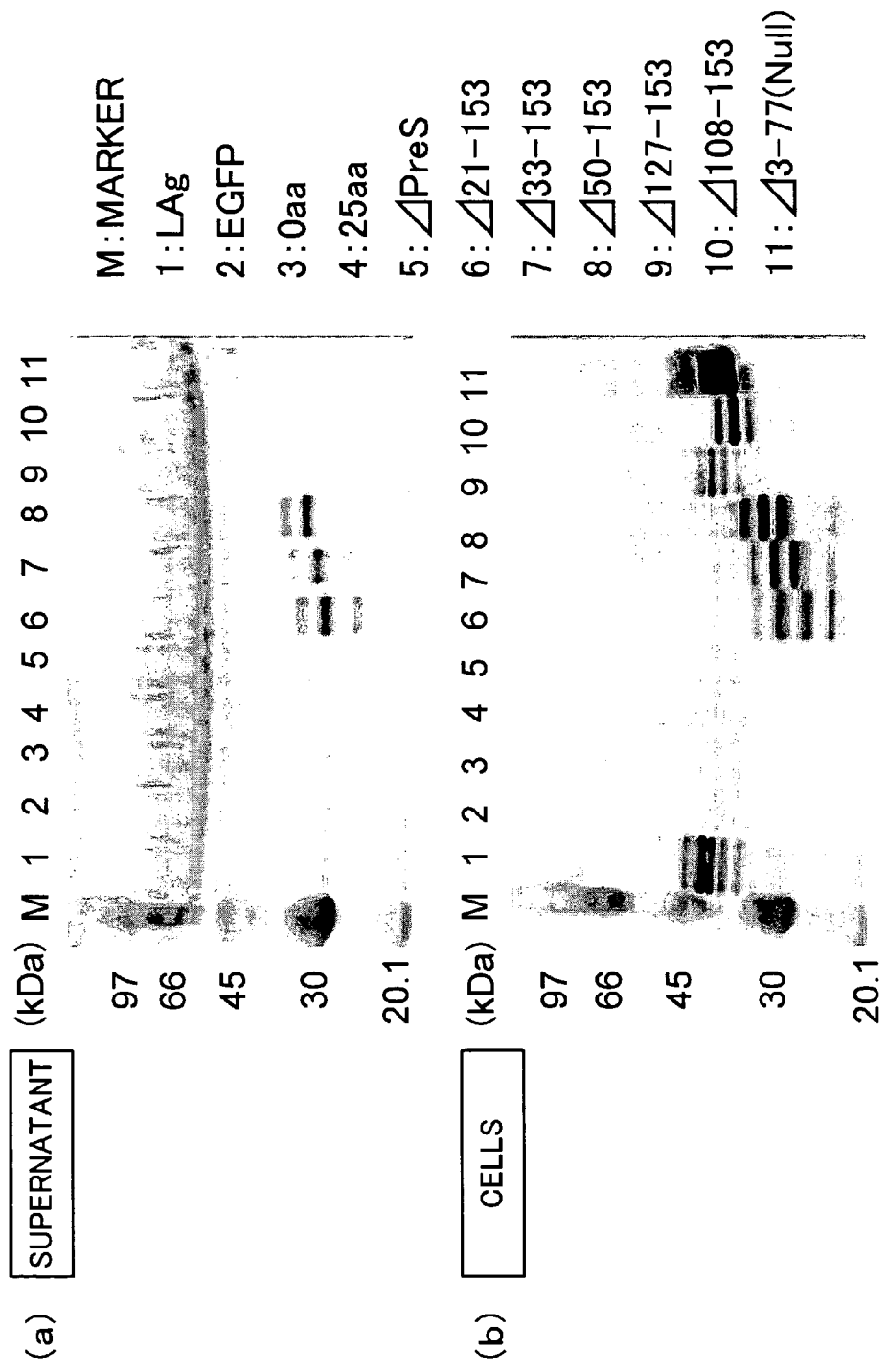
FIG. 18 is a diagram showing results of SDS-PAGE performed on the deletion HBsAg protein expressed in FIGS. 16(a) and 16(b), wherein (a) is a result in supernatant, and (b) is a result in cells.
Figure 19:
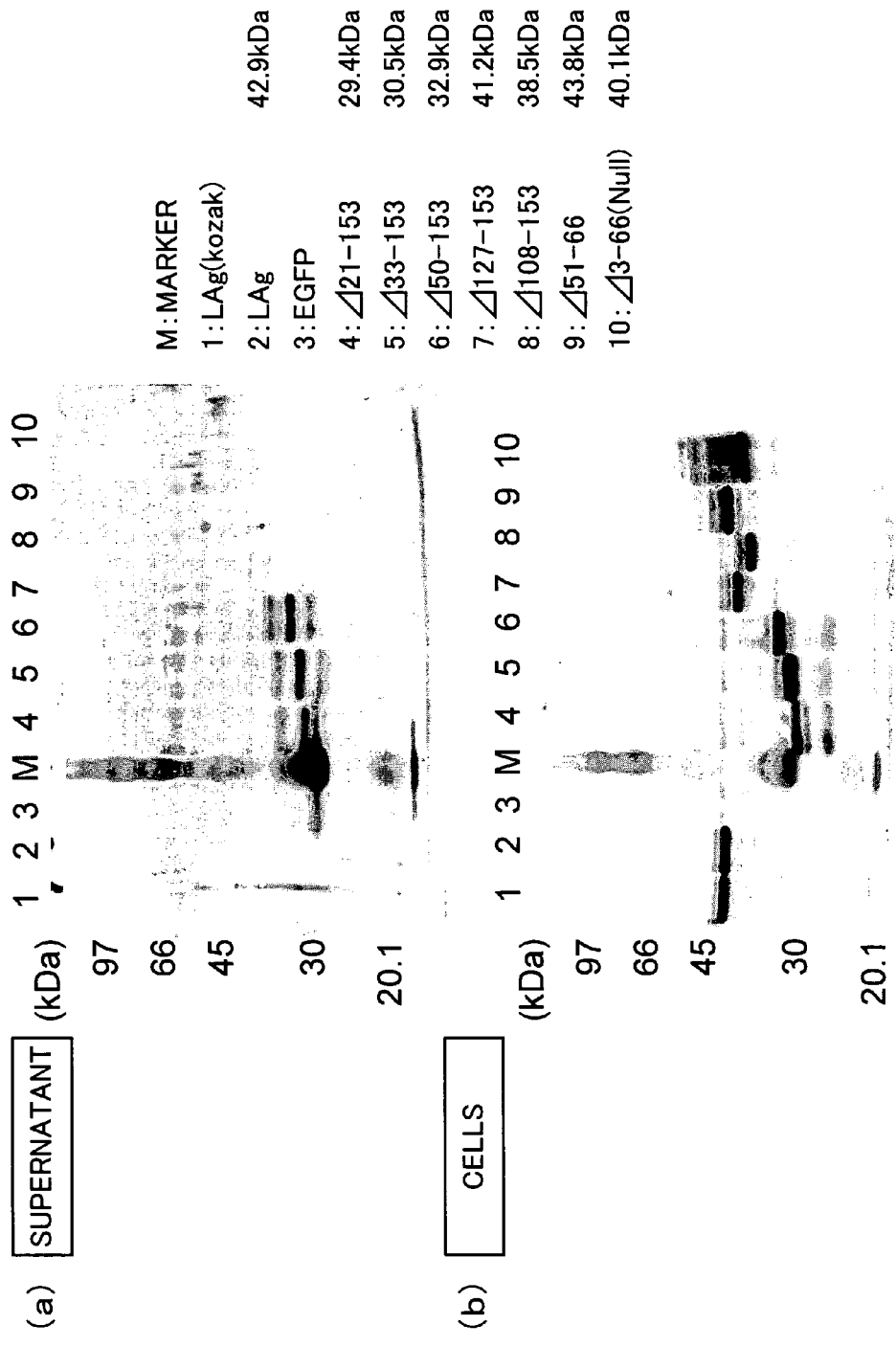
FIG. 19 is a diagram showing results of Western blotting performed on the deletion HBsAg protein expressed in FIGS. 16(a) and 16(b), wherein (a) is a result in supernatant, and (b) is a result in cells.

The level of expression was also measured by SDS-PAGE and Western blotting, as shown in FIG. 18 and FIG. 19. As the primary antibody, a mouse anti-S protein antibody (prepared by the inventors) was used. The anti-mouse IgG antibody AP tag (Promega) was used as the secondary antibody. Note that, FIG. 19 shows the result of Western blotting after enzyme treatment (EndH), which was performed to remove N-sugar chains. The result is shown along with the molecular weights. The EndH treatment revealed that the Pre-S region of the product mutant L particles had N-sugar chains. For Δ51-66 in FIG. 19, a plasmid prepared with the primers of SEQ ID NOs: 25 and 26 were used according to the method described in Example F-1.

The experiment showed that the level of protein expression was particularly desirable in the deletion HBsAg L proteins (a) through (c).

Example F-3

Preparation of Deletion HBsAg L Proteins with Inserted Epithelial Growth Factor (EGF)

Using the deletion HBsAg L protein expression genes (a) through (c) (Δ21-153, Δ33-153, and Δ50-153) which showed desirable levels of protein expression, the EGF gene was inserted in these genes at the NotI sites and expressed therein. The EGF gene was obtained by cleaving the pGLDLIIP39-RcT-EGF (prepared by the inventors) with the restriction enzyme NotI. The resulting plasmid was used to transform the Cos7 cells. After 24 hr incubation in serum media, the samples were further incubated for 3 days on serum-free media. The culture media were collected and concentrated with an ultrafilter, so as to obtain mutant L particles (deletion HBsAg L proteins (a) through (c)).

The green fluorescent protein expression plasmid (pEGFP-F (Clontech)) was electroporated in the particles of the respective proteins, and the GFP expression plasmid was encapsulated in the particles. The resulting particles were used in a gene transfer experiment using hepatocyte HepG2 and epithelial cell A431. Observation of the GFP fluorescence showed that specificity to the hepatocyte HepG2 had been lost, and that binding to the epithelial cell A431 was highly selective. That is, the experiment successfully retargeted the epithelial cell A431.

Example F-4

Preparation of Deletion HBsAg L Protein by Transformation in Yeast Cells

Genes that express the deletion HBsAg L proteins Δ21-153, Δ33-153, and Δ50-153 (proteins (a) through (c)) which showed desirable levels of protein expression in Cos7 cells were obtained by cleaving the plasmid at the XhoI sites. The genes so obtained were inserted at the XhoI sites of the yeast expressed plasmids pGLDLIIP39-RcT (see FIG. 20), which were then transferred to S. cerevisiae AH22R$^-$ strain by a spheroplast method. The transformants were incubated for 3 days in industrial media High-Pi and another 3 days in 8S5N-P400 media. The cultured cells were collected and disrupted with glass beads. Then, the cell extract was measured to confirm antigenicity and the level of expression. Antigenicity was measured with a cultured yeast enzyme immunoassay device IMx (Dainabot Co. Ltd.), and the level of protein expression was measured by SDS-PAGE and Western blotting (using anti-S protein antibody as the primary antibody, and AP tagged anti-mouse IgG antibody as the secondary antibody) (see FIG. 21 and FIG. 22).

Figure 20:
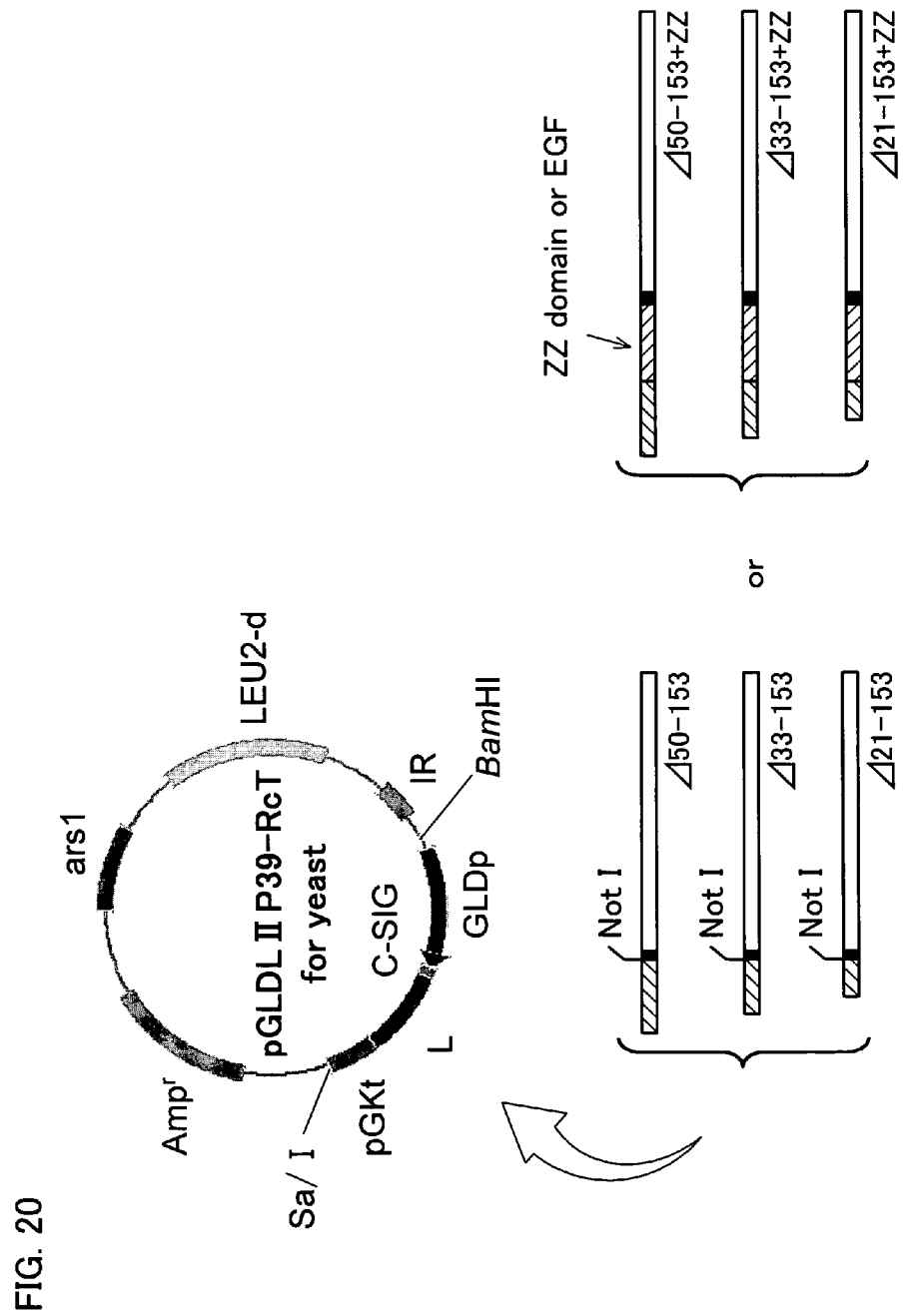
FIG. 20 is a schematic diagram illustrating deletion HBsAg protein expression genes transferred into yeasts, and a plasmid into which the genes are transferred, as described in Examples of the present invention.
Figures 21, 22:
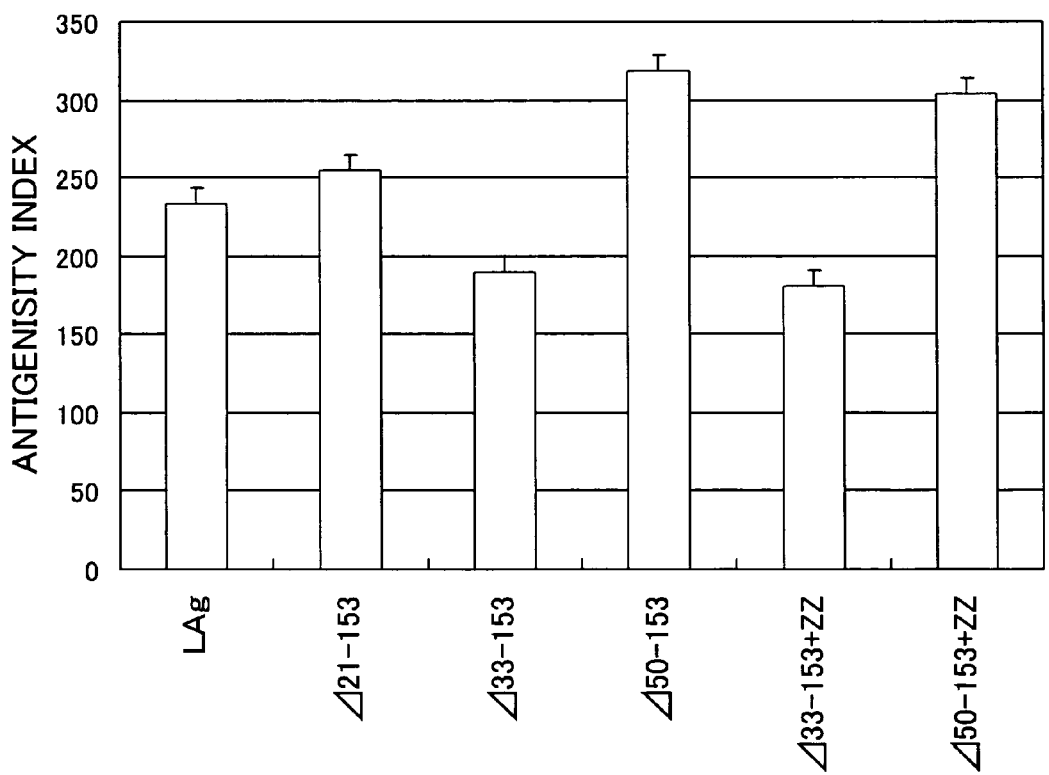
FIG. 21 is a diagram showing a result of enzyme immunoassay in data form, confirming the expression of deletion HBsAg L protein using the plasmid of FIG. 20.
FIG. 22 is a graph representing a result of enzyme immunoassay, confirming the expression of deletion HBsAg L protein using the plasmid of FIG. 20.

Additionally, two kinds of plasmids were constructed using the NotI sites: a plasmid for displaying a ZZ domain gene of protein A; and a plasmid for displaying EGF (see FIG. 20). In sum, the following plasmids were constructed (expression plasmid for efficiently expressing deletion HBsAg L protein in yeasts): pGLDLIIP39-RcT-Δ50-153; pGLDLIIP39-RcT-Δ33-153, pGLDLIIP39-RcT-Δ21-153; pGLDLIIP39-RcT-Δ50-153-ZZ; pGLDLIIP39-RcT-Δ33-153-ZZ; pGLDLIIP39-RcT-Δ21-153-ZZ; pGLDLIIP39-RcT-Δ50-153-EGF; pGLDLIIP39-RcT-Δ33-153-EGF; and pGLDLIIP39-RcT-Δ21-153-EGF. In addition, pGLDLIIP39-RcT-Δ3-66 was constructed as a control. These yeast-expressed plasmids were transferred into S. cerevisiae AH22R$^-$ strain by a spheroplast method. The transformants were incubated for 3 days in industrial media High-Pi and another 3 days in 8S5N-P400 media. The cultured cells were collected and disrupted with glass beads, and the cell extract was measured to confirm the level of protein expression by measuring antigenicity with a cultured yeast enzyme immunoassay device IMx (Dainabot Co. Ltd.) (see FIG. 21 and FIG. 22).

The enzyme immunoassay confirmed formation of deletion particles. The levels of antigenicity for the deletion HBsAg L proteins (deletion HBsAg particles) Δ21-153, Δ33-153, and Δ50-153 compared to that of wild-type particles (LAg in the drawings) (see FIG. 21 and FIG. 22). The deletion HBsAg particles A3-66 used as a control produced no transformant (not shown). The deletion HBsAg particles Δ50-153 are particularly advantageous since its level of protein expression, combined with a considerably large amount of deletion HBsAg particles displaying a ZZ domain (Δ50-153+ZZ), exceeds that of the wild-type.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, the present invention provides a drug whose particle surface displays an antibody such as a cancer specific antibody. The drug can be used by a convenient method of intravenous injection to specifically and effectively treat specific diseased cells or tissues. The invention is a great leap forward from conventional gene therapy in that it does not require any surgical operation, and that the risk of side effect is greatly reduced. The drug is therefore usable in clinical applications in its present form.

---

The invention claimed is:

1. A hollow nanoparticle for delivering a substance to a cell, comprising a modified HBV surface antigen large (HBsAg L) protein formed into a particle, an antibody displayed on the surface of the particle, and a substance encapsulated inside the particle, wherein the modified HBsAg L protein includes a replacement of amino acids 50 to 153 in a pre-S region of the HBsAg L protein, corresponding to HBV serotype y, by a ZZ tag consisting of SEQ ID NO: 29, and wherein the antibody binds to the ZZ tag fused to the HBsAg L protein.

2. The hollow nanoparticle of claim 1, wherein the antibody is a single chain antibody.

3. The hollow nanoparticle of claim 1, wherein the modified HBsAg L protein is expressed in a eukaryotic cell.

4. The hollow nanoparticle of claim 3, wherein the eukaryotic cell is selected from a group consisting of a yeast cell, an insect cell, and an animal cell.

5. The hollow nanoparticle of claim 1, wherein the substance comprises a gene.

6. The hollow nanoparticle of claim 5, wherein the gene comprises a gene of thymidine kinase derived from simplex herpes virus.

7. A hollow nanoparticle comprising a modified HBV surface antigen large (HBsAg L) protein formed into a particle, wherein the modified HBsAg L protein includes a replacement of amino acids 50 to 153 in a pre-S region of the HBsAg L protein, corresponding to HBV serotype y, by a ZZ tag consisting of SEQ ID NO: 29.

* * * * *

SEQUENCE LISTING

```
<160> NUMBER OF SEQ ID NOS: 29

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 1
cgacaaggca tgggaggcgg ccgcagccct caggctcag                              39

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 2
ctgagcctga gggctgcggc cgcctcccat gccttgtcg                              39

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 3
ggggacctcg gatccgcgag cttaccagtt ctcaca                                 36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 4
gaggtcgacc agctttaacg aacgcagaat tttcga                                 36

<210> SEQ ID NO 5
```

-continued

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 5
ggccgctgga gccacccgca gttcgaaaaa ggc                                33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 6
ggccgccttt ttcgaactgc gggtggctcc agc                                33

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 7
ggggtaccat gagatctttg ttgatcttg                                     29

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 8
ggccgcggtt aaatgtatac ccaaagac                                      28

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 9
gggggcggcc gcgcgcaaca cgatgaagcc gtagac                             36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 10
ggttgagata aaagagcttt tggcgcggcc gcctttt                            36

<210> SEQ ID NO 11
<211> LENGTH: 36
<212> TYPE: DNA

<213> ORGANISM: Artificial Sequence
<220> FEATURE:
<223> OTHER INFORMATION: Description of Artificial Sequence:Artificially
    synthesized sequence

<400> SEQUENCE: 11
gggggcggcc gcgatattga tatgacccaa tctcca                         36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:Artificially
    synthesized sequence

<400> SEQUENCE: 12
cccgcggccg cccgaggaga cggtgactga ggtccc                         36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:Artificially
    synthesized sequence

<400> SEQUENCE: 13
gggggcggcc gcgatgtgca gcttcaggag tcggga                         36

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Artificially
    synthesized sequence

<400> SEQUENCE: 14
ggggcggccg cctttttattt ccaactttgt                               30

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:Artificially
    synthesized sequence

<400> SEQUENCE: 15
ccagttggac ggcggccgcc ctgcaccgaa c                              31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:Artificially
    synthesized sequence

<400> SEQUENCE: 16
gttcggtgca gggcggccgc cgtccaactg g                              31

<210> SEQ ID NO 17
<211> LENGTH: 34
<212> TYPE: DNA
<213> ORGANISM: Artificial Sequence
<220> FEATURE:

<223> OTHER INFORMATION: Description of Artificial Sequence:Artificially
      synthesized sequence

<400> SEQUENCE: 17
caatccagat tggggcggcc gccctgcacc gaac                                     34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 18
gttcggtgca gggcggccgc cccaatctgg attg                                     34

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 19
ggtaggagcg ggcggccgcc ctgcaccgaa c                                        31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 20
gttcggtgca gggcggccgc ccgctcctac c                                        31

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 21
cctcaggccg gcggccgccc tgcaccgaac                                          30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 22
gttcggtgca gggcggccgc cctgaggatg                                          30

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence -continued

<400> SEQUENCE: 23
cagagtgagg ggcggccgcc ctgcaccgaa c                                          31

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 24
gttcggtgca gggcggccgc ccctcactct g                                          31

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 25
ggtaggagcg ggcggccgca gccctcaggc                                            30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized sequence

<400> SEQUENCE: 26 gcctgaggg ctgcggccgcc cgctcctacc                                            30

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence:Artificially
      synthesized sequence

<400> SEQUENCE: 27

Ser Ala Trp Arg His Pro Gln Phe Gly Gly
 1               5                  10

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:Artificially
      synthesized sequence

<400> SEQUENCE: 28

Trp Ser His Pro Gln Phe Glu Lys
 1               5

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence:Artificially
      synthesized sequence

```
<400> SEQUENCE: 29

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Val Asp Asn Lys Phe Asn
50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
            115
```